(12) United States Patent
Kim et al.

(10) Patent No.: US 10,591,714 B2
(45) Date of Patent: Mar. 17, 2020

(54) ENDOSCOPIC APPARATUS FOR THERMAL DISTRIBUTION MONITORING

(71) Applicant: ELECTRONICS AND TELECOMMUNICATIONS RESEARCH INSTITUTE, Daejeon (KR)

(72) Inventors: Keo Sik Kim, Gwangju (KR); Hyun Seo Kang, Gwangju (KR); Sung Chang Kim, Gwangju (KR); Young Sun Kim, Gwangju (KR); Jeong Eun Kim, Gwangju (KR); Hee Seung Kim, Gwangju (KR); Ji Hyoung Ryu, Jeonju-si (KR); Hyoung Jun Park, Gwangju (KR); Dong Hoon Son, Gwangju (KR); Chan Il Yeo, Gwangju (KR); Young Soon Heo, Gwangju (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 72 days.

(21) Appl. No.: 15/610,010

(22) Filed: May 31, 2017

(65) Prior Publication Data

US 2018/0067299 A1 Mar. 8, 2018

(30) Foreign Application Priority Data

Sep. 7, 2016 (KR) ........................ 10-2016-0115036

(51) Int. Cl.
*H04N 5/33* (2006.01)
*G02B 23/24* (2006.01)
(Continued)

(52) U.S. Cl.
CPC ........ *G02B 23/2484* (2013.01); *A61B 1/0005* (2013.01); *A61B 1/045* (2013.01);
(Continued)

(58) Field of Classification Search
CPC .............. G02B 23/2484; G02B 23/243; G02B 23/2469; G02B 27/30; G02B 27/106;
(Continued)

(56) References Cited

U.S. PATENT DOCUMENTS 4,953,539 A * 9/1990 Nakamura ......... A61B 1/00177
348/E5.029
RE34,411 E * 10/1993 Nishioka .................. A61B 1/05
348/70
(Continued)

FOREIGN PATENT DOCUMENTS

JP 2003-018467 A 1/2003
KR 10-2005-0113442 A 12/2005
(Continued)

*Primary Examiner* — Neil R Mikeska
(74) *Attorney, Agent, or Firm* — Rabin & Berdo, P.C.

(57) ABSTRACT

Provided is an endoscopic apparatus for thermal distribution monitoring, and more particularly, an endoscopic apparatus for thermal distribution monitoring that is capable of providing a functional image in which various images such as a real image and a thermal image, are matched to one another. The endoscopic apparatus includes: an image collecting unit including a thermal image collecting unit collecting a thermal image from an image signal of an object and a real image collecting unit collecting a real image from the image signal of the object; a controller transmitting a control signal to the image collecting unit so as to transmit the image signal to one of the thermal image collecting unit and the real image collecting unit according to a preset period; and a display displaying the collected thermal image and real image.

17 Claims, 25 Drawing Sheets

(51) Int. Cl.
*H04N 5/225* (2006.01)
*A61B 5/00* (2006.01)
*A61B 1/045* (2006.01)
*G02B 23/12* (2006.01)
*A61B 1/00* (2006.01)
*A61B 5/01* (2006.01)

(52) U.S. Cl.
CPC ............ *A61B 5/0086* (2013.01); *A61B 5/015* (2013.01); *G02B 23/12* (2013.01); *H04N 5/2256* (2013.01); *H04N 5/2258* (2013.01); *H04N 5/332* (2013.01); *A61B 5/0035* (2013.01); *H04N 2005/2255* (2013.01)

(58) Field of Classification Search
CPC .... H04N 5/332; H04N 5/2256; H04N 5/2258; A61B 1/04; A61B 1/00045; A61B 1/07; A61B 1/00126; A61B 1/00027
See application file for complete search history.

(56) References Cited

U.S. PATENT DOCUMENTS

| | | | | |
|---|---|---|---|---|
| 5,255,087 | A * | 10/1993 | Nakamura | A61B 1/05 348/164 |
| 6,652,452 | B1 | 11/2003 | Seifert et al. | |
| 9,678,331 | B1 * | 6/2017 | Miller | G02B 26/0816 |
| 2001/0008460 | A1 * | 7/2001 | Yamawaki | G02B 21/082 359/350 |
| 2002/0022766 | A1 * | 2/2002 | Adachi | A61B 1/00009 600/160 |
| 2002/0138008 | A1 * | 9/2002 | Tsujita | A61B 1/00009 600/473 |
| 2003/0068164 | A1 * | 4/2003 | Nanjyo | A61B 3/12 396/18 |
| 2003/0174279 | A1 * | 9/2003 | Kobayashi | A61B 3/14 351/200 |
| 2005/0122475 | A1 * | 6/2005 | Vilser | A61B 3/1241 351/221 |
| 2007/0232861 | A1 * | 10/2007 | Kohno | A61B 1/0638 600/160 |
| 2009/0264768 | A1 * | 10/2009 | Courtney | A61B 5/0062 600/463 |
| 2012/0130175 | A1 * | 5/2012 | Koshikawa | A61B 1/0638 600/178 |
| 2012/0133729 | A1 * | 5/2012 | Strzempko | B63G 8/38 348/36 |
| 2013/0258284 | A1 * | 10/2013 | Makihira | A61B 3/14 351/206 |
| 2014/0066781 | A1 | 3/2014 | Park et al. | |
| 2014/0081126 | A1 | 3/2014 | Kim et al. | |
| 2014/0194748 | A1 * | 7/2014 | Yamamoto | A61B 5/0059 600/473 |
| 2015/0282749 | A1 * | 10/2015 | Zand | A61B 5/0071 600/301 |
| 2016/0286197 | A1 * | 9/2016 | Schwarz | A61B 1/00096 |

FOREIGN PATENT DOCUMENTS

| | | |
|---|---|---|
| KR | 10-2007-0071556 A | 7/2007 |
| KR | 10-2012-0058341 A | 6/2012 |
| KR | 10-2012-0097564 A | 9/2012 |
| KR | 101332716 B1 | 11/2013 |
| KR | 10-2014-0046623 A | 4/2014 |

\* cited by examiner

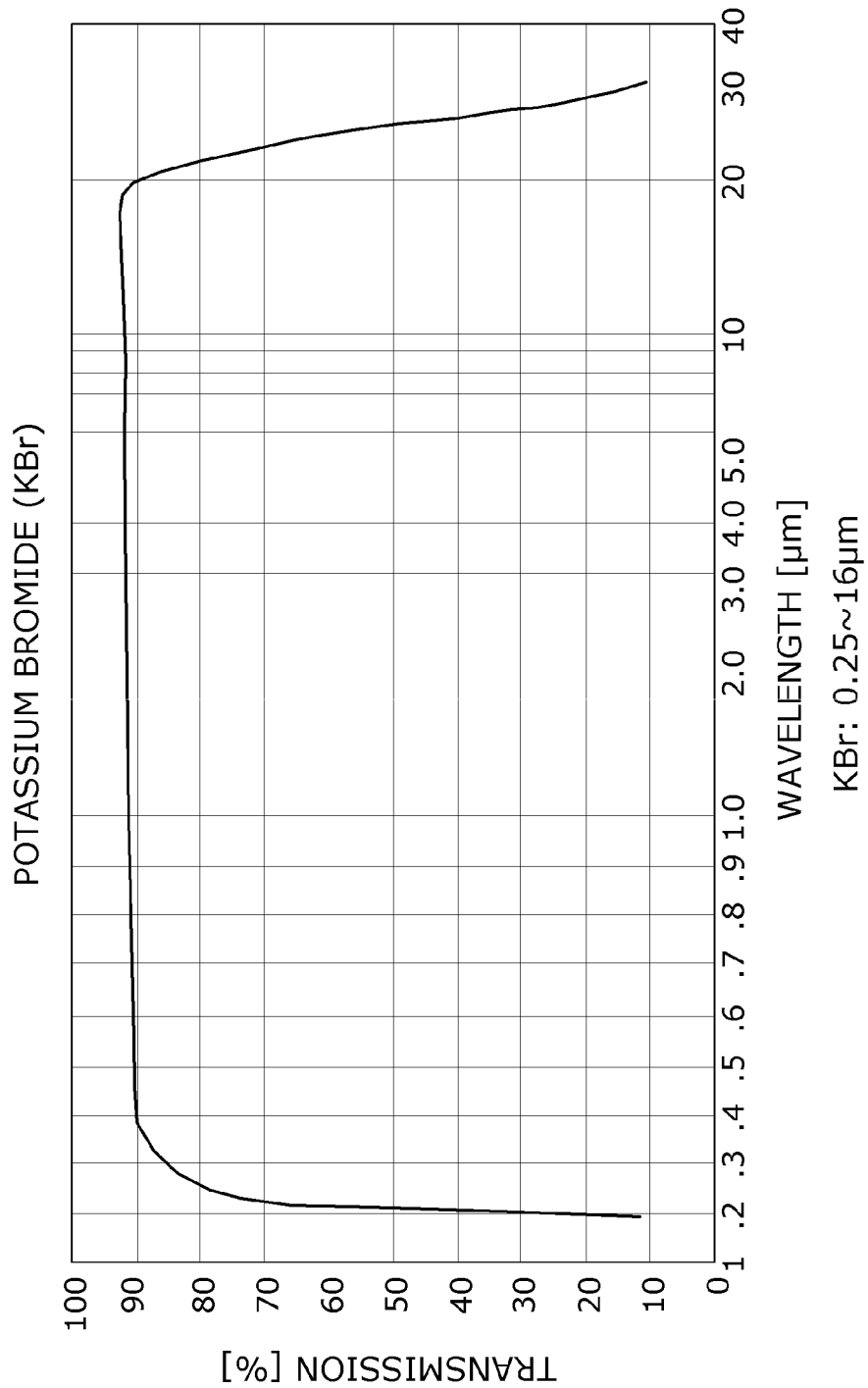

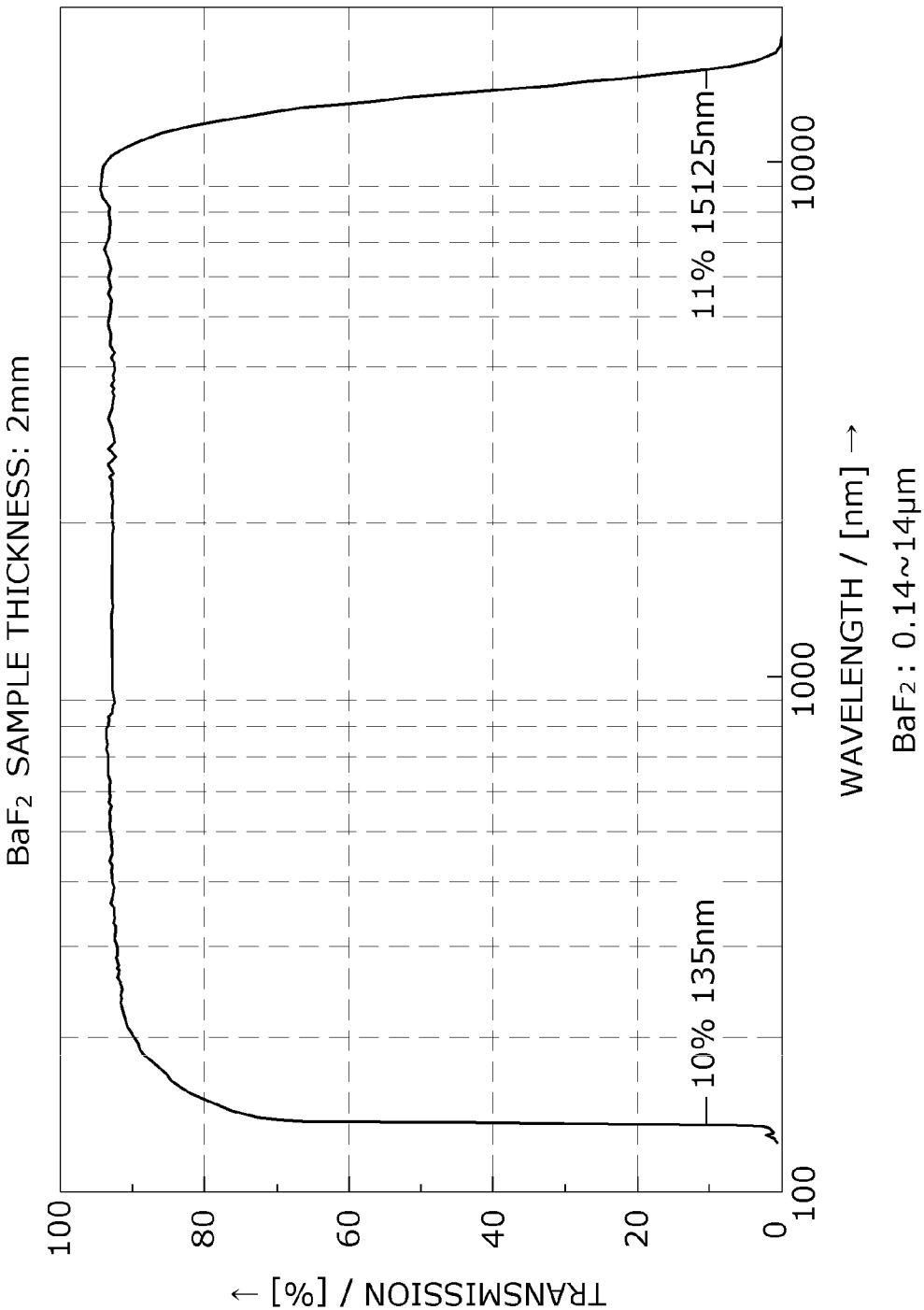

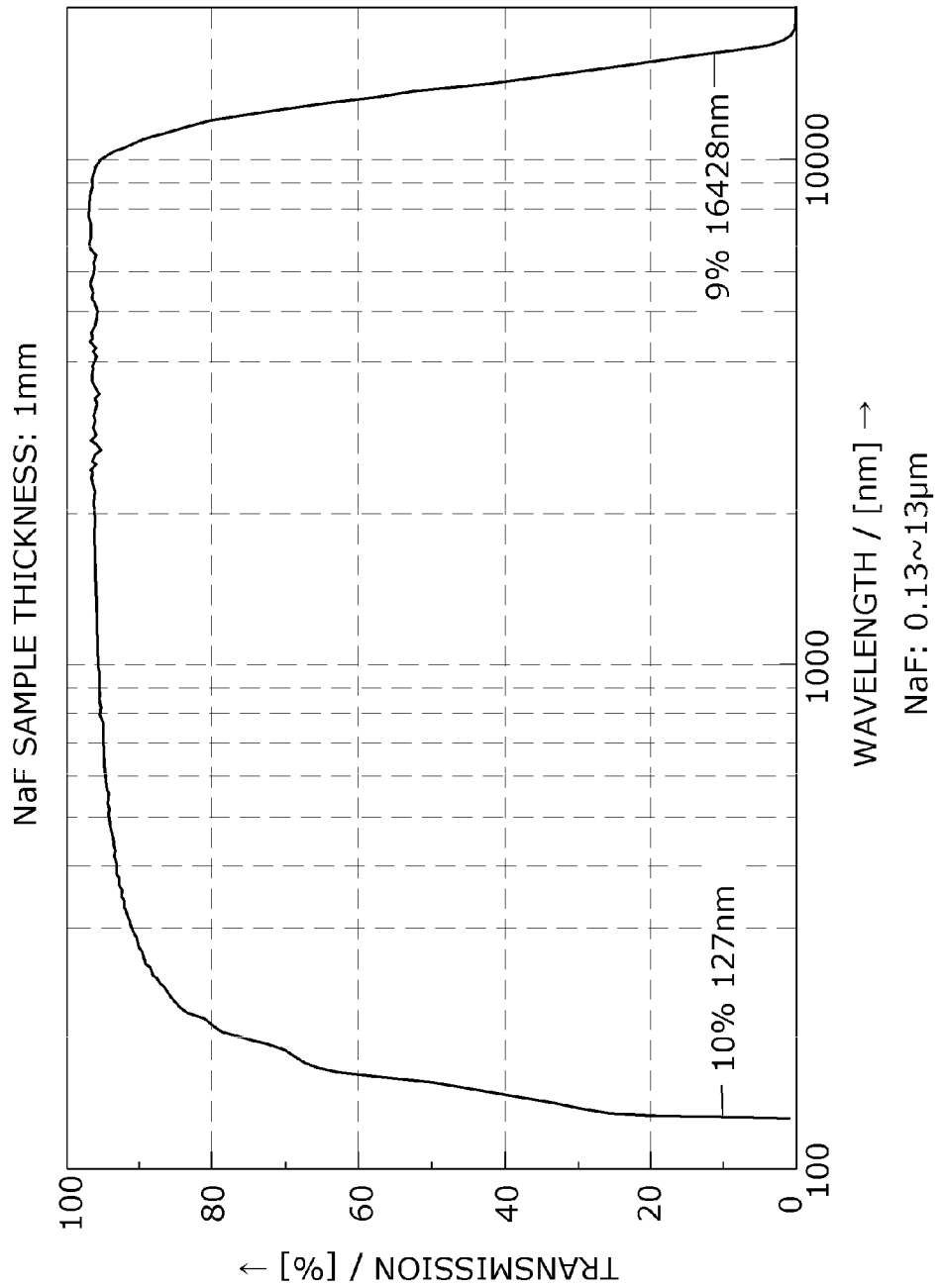

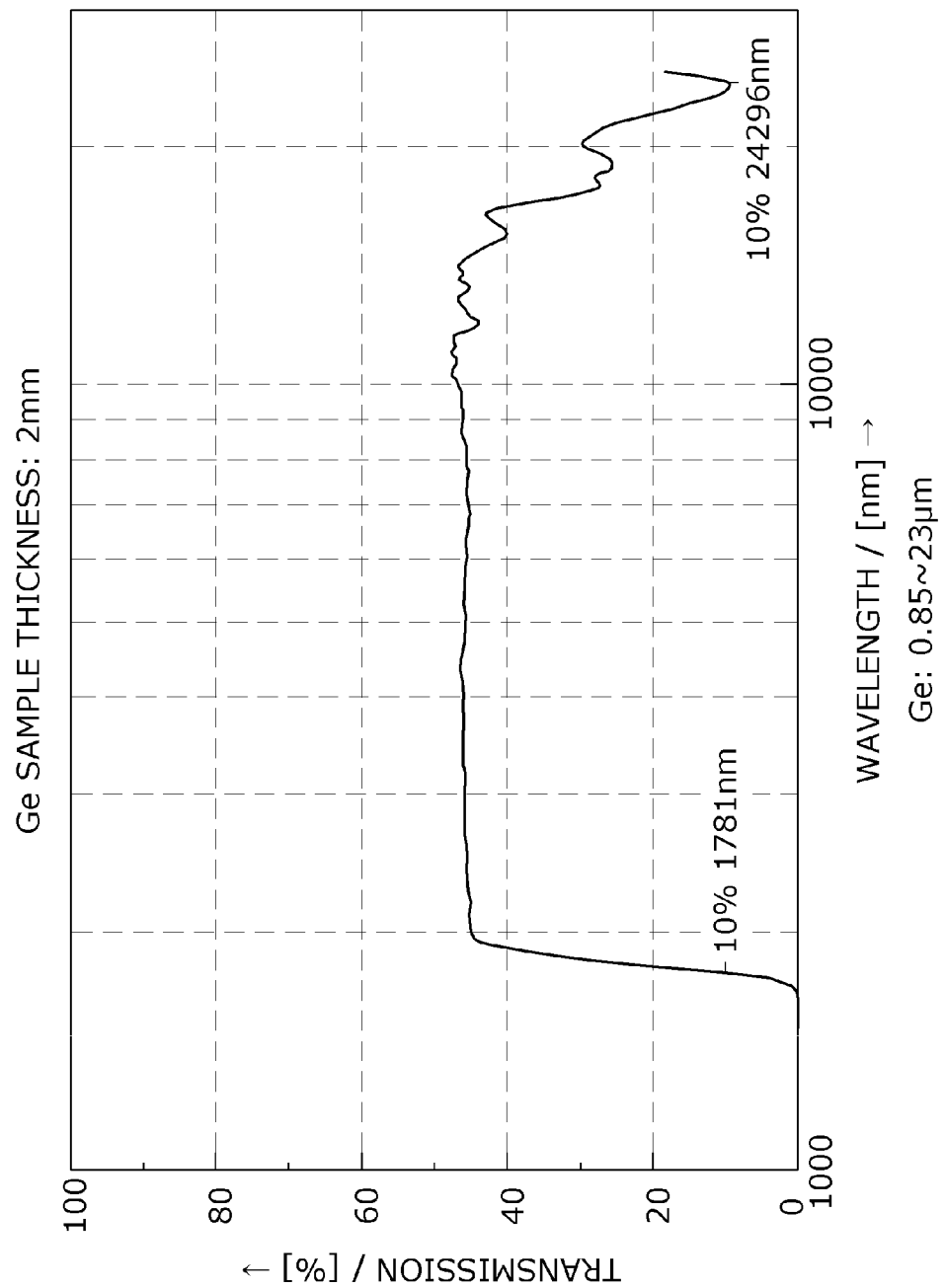

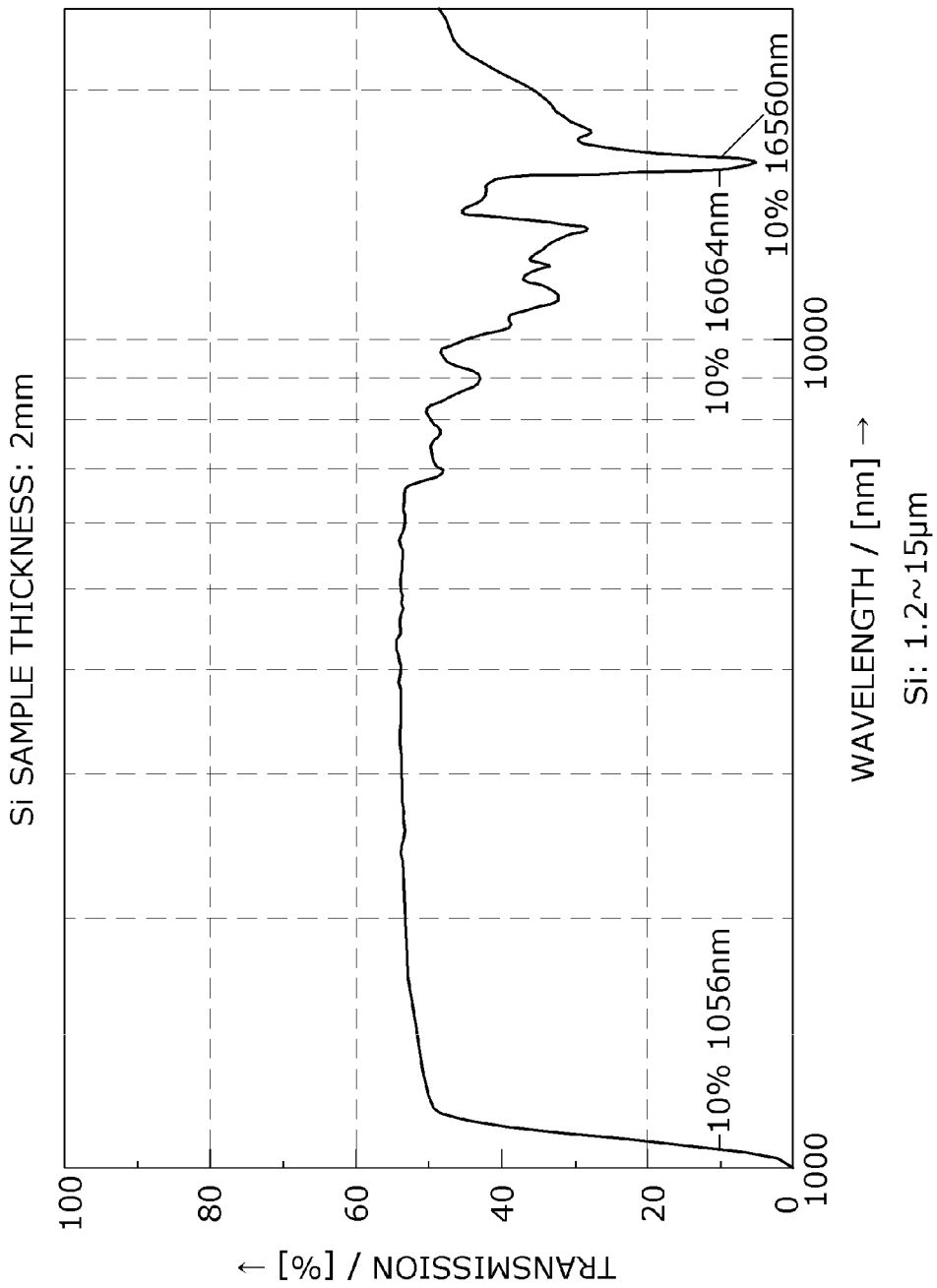

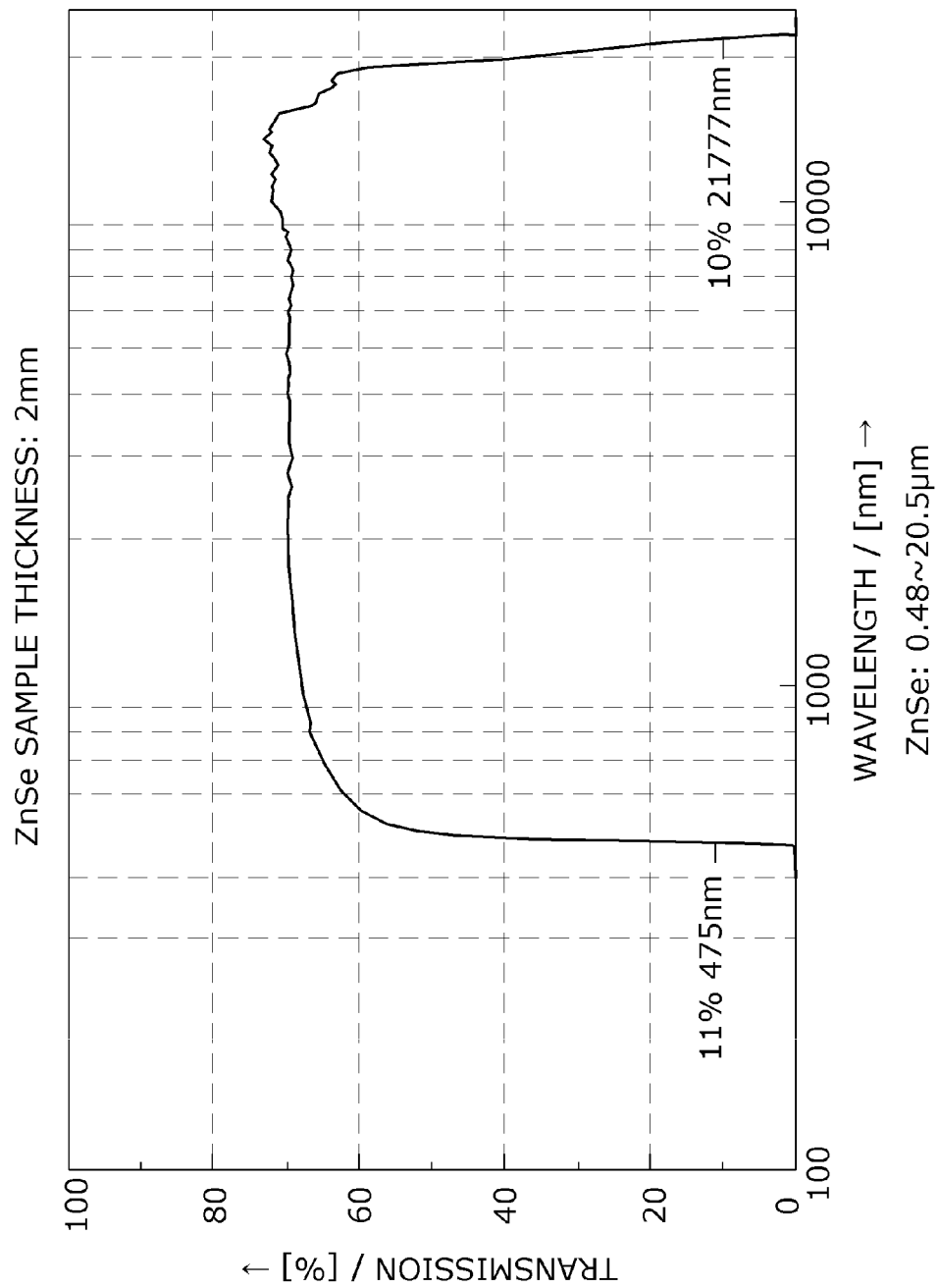

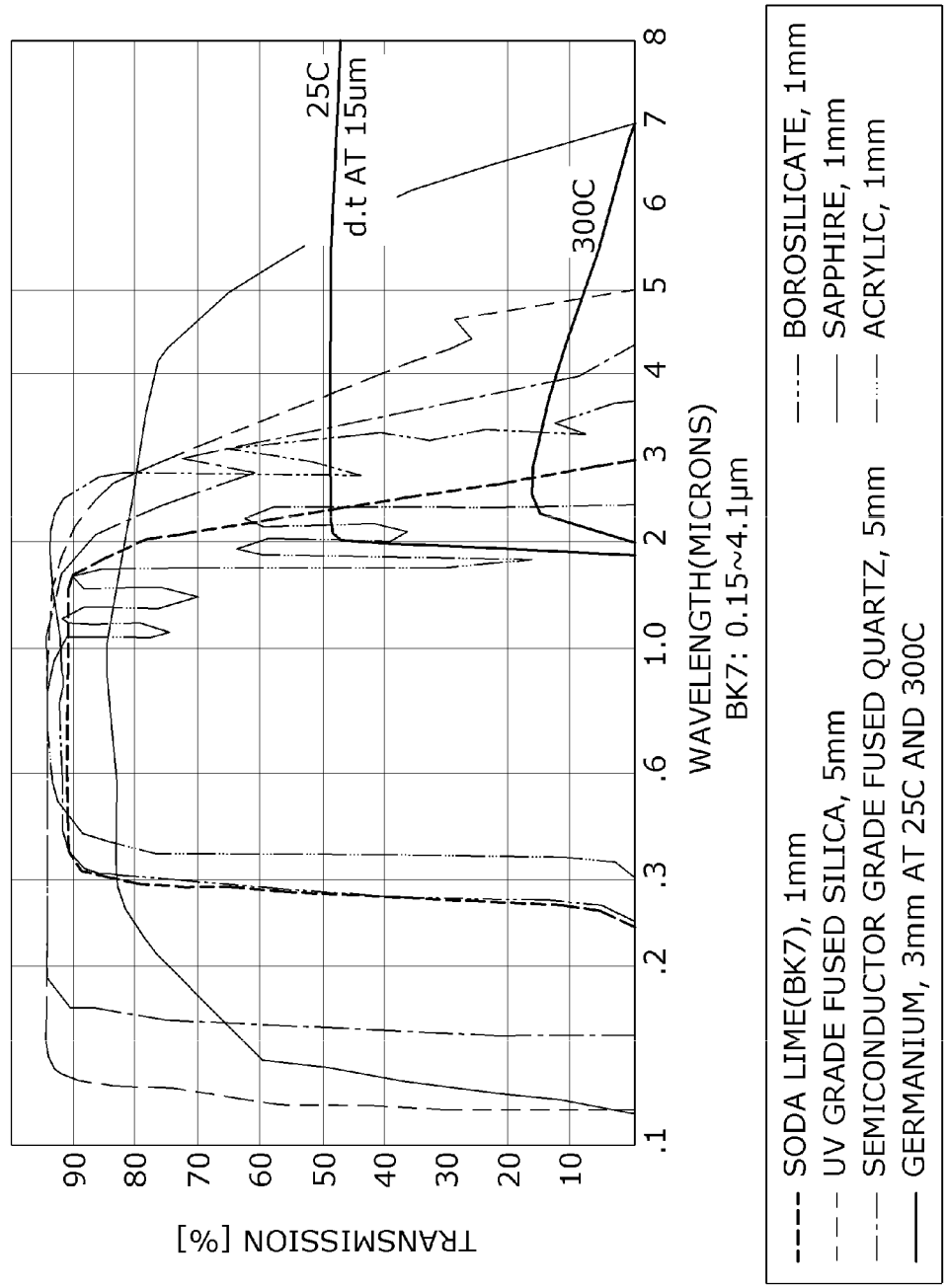

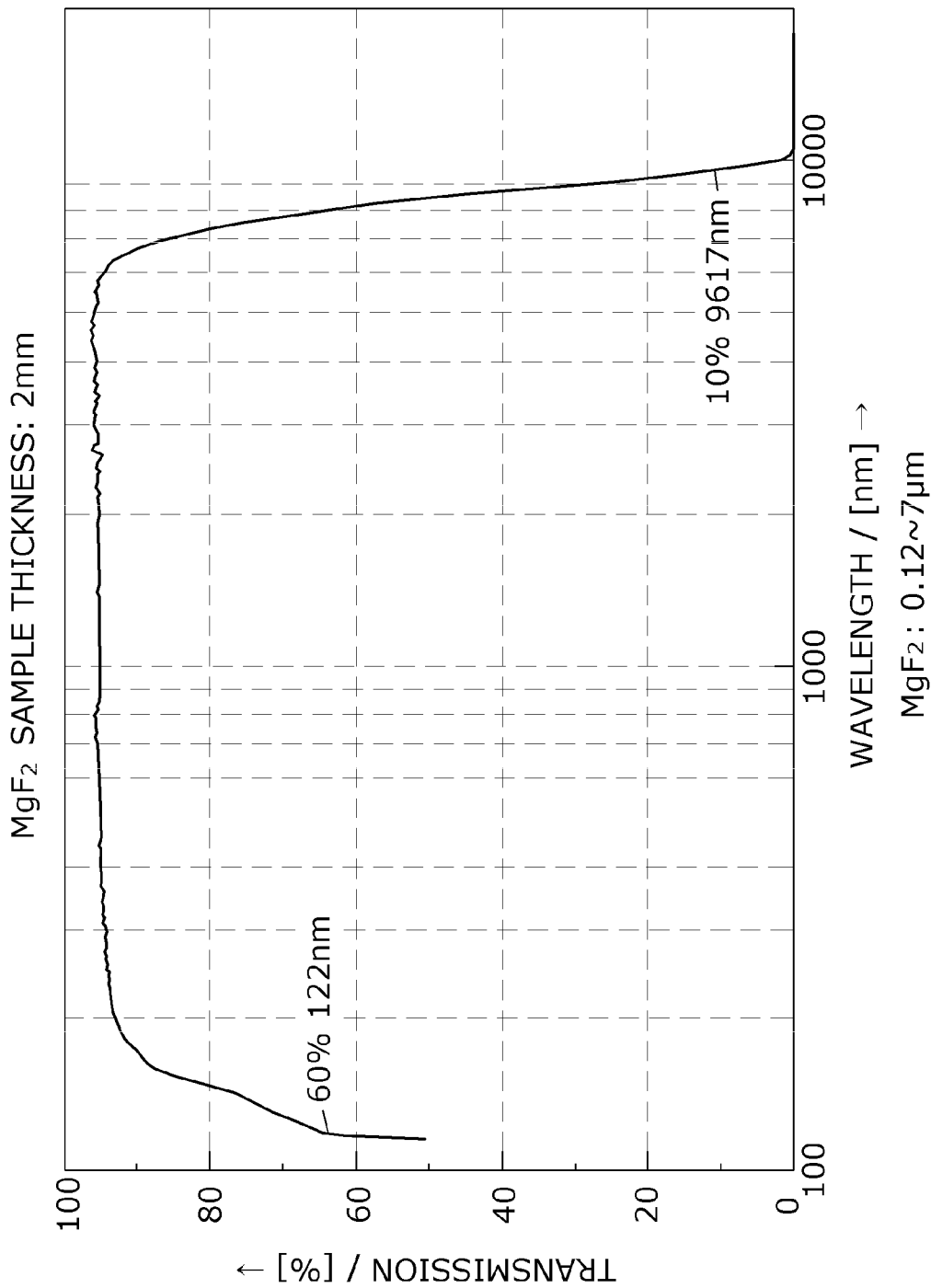

ENDOSCOPIC APPARATUS FOR THERMAL DISTRIBUTION MONITORING

CROSS-REFERENCE TO RELATED APPLICATION

This application claims priority to and the benefit of Korean Patent Application No. 2016-0115036, filed on Sep. 7, 2016, the disclosure of which is incorporated herein by reference in its entirety.

BACKGROUND

1. Field of the Invention

The present invention relates to an endoscopic apparatus for thermal distribution monitoring, and more particularly, to an endoscopic apparatus for thermal distribution monitoring that is capable of providing a functional image in which various images such as a real image and a thermal image, are matched to one another.

2. Discussion of Related Art

A thermal distribution monitoring is a technology, whereby a photon in a band of infrared (IR) rays emitted from a surface of an object is collected by using an infrared image sensor and then is analyzed to acquire information about thermal distribution. The thermal distribution monitoring technology is used not only to do early diagnosis for quickly detecting carrier suspects when an acute infectious disease (ex. Severe Acute Respiratory Syndrome (SARS), Middle East Respiratory Syndrome Coronavirus (MERS-CoV), etc.) occurs, but also to do a screening test on local part lesion (ex. rheumatoid arthritis, Raynaud syndrome, breast cancer, etc.) in a medical field. Also, the thermal distribution monitoring technology is widely used in structure safety diagnosis or a non-destructive quality test, etc. in an industrial field.

However, because a conventional thermal image apparatus uses large-area information acquired from the surface of the object, accuracy of diagnosis is lowered, and a thermal image system probe structure is bulky such that a diagnosis part is limited. Also, there are limitations in acquiring thermal distribution information inside a human body, such as the inside of an ear, the inside of noise, the inside of the abdominal cavity, etc.

Meanwhile, because edema, bleeding, etc. are diagnosed by the naked eye by using a laryngoscope (throat), an otoscope (ear), and an ophthalmoscope (eye), etc. in an ear-nose-throat (ENT) clinic and an ophthalmic clinic, etc., the result of diagnosis may vary according to an inspector's subjective opinion. A thermal image monitoring function is added to an apparatus having an endoscopic shape that is capable of acquiring information about a cavity (ex. the inside of an ear, the inside of noise, the larynx, the abdominal cavity, etc.) inside the human body such that a real image and a thermal image can be simultaneously observed and thus more objective and precise diagnosis can be carried out.

SUMMARY OF THE INVENTION

The present invention is directed to an endoscopic apparatus that is capable of simultaneously observing a real image and a thermal image inside an object by adding a thermal image monitoring function to the endoscopic apparatus capable of observing the inside of the object (human body or a building).

The present invention is also directed to an endoscopic apparatus on which a tube (scope) as an internal insertion tool can be easily mounted so that internal insertion and observation can be easily performed on an object.

According to an aspect of the present invention, there is provided an endoscopic apparatus including: an image collecting unit including a thermal image collecting unit collecting a thermal image from an image signal of an object and a real image collecting unit collecting a real image from the image signal of the object; a controller transmitting a control signal to the image collecting unit so as to transmit the image signal to one of the thermal image collecting unit and the real image collecting unit according to a preset period; and a display displaying the collected thermal image and real image.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 3A to FIG. 3F is a view showing transmission curves of several materials having good transmission characteristics in a visible ray band and in an infrared band, respectively;

FIG. 8A to FIG. 8C is a view showing transmission curves of several materials having good transmission characteristics in the infrared band;

FIG. 9A to FIG. 9F is a view showing transmission curves of several materials having good transmission characteristics in the visible ray band;

DETAILED DESCRIPTION OF EXEMPLARY EMBODIMENTS

In the description of embodiments of the present invention, if it is determined that a detailed description of known configurations or functions related to the invention may obscure the subject matter of the invention, the detailed description will be omitted.

An expression used herein such as "include" or "may include" etc. indicates the existence of the functions, actions, or components disclosed in the specification, and are not intended to limit one or more additional functions, actions, or components. In addition, in the present specification, it is to be understood that the terms such as "including" or "having," etc. are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

An expression used in the singular encompasses the expression of the plural, unless it has a clearly different meaning in the context.

Hereinafter, the present invention will be described with reference to the attached drawings.

The present invention provides an endoscopic apparatus that is capable of splitting an image signal (light signal) on an object observed using one tube (scope) by using an optomechanical device inside an endoscope into a visible ray sensor and an infrared sensor so that a real image and a thermal image can be sequentially acquired, a two-dimensional image inside the object can be taken and thermal distribution monitoring can be performed.

In various embodiments of the present invention, in the endoscopic apparatus, a Galvanometer in which a reflector and a motor are coupled to each other, is used to split the image signal, and the split image signal can be transmitted to the visible ray sensor and the infrared sensor, respectively.

Also, in various embodiments of the present invention, the endoscopic apparatus includes an illumination unit having the same optical path as that of an image collecting unit so as to increase brightness of the real image after the illumination unit is inserted into the object. Thus, the diameter of a tube (scope) that is an internal insertion tool can be reduced, and internal insertion and observation of the object can be easily performed.

Figure 1:
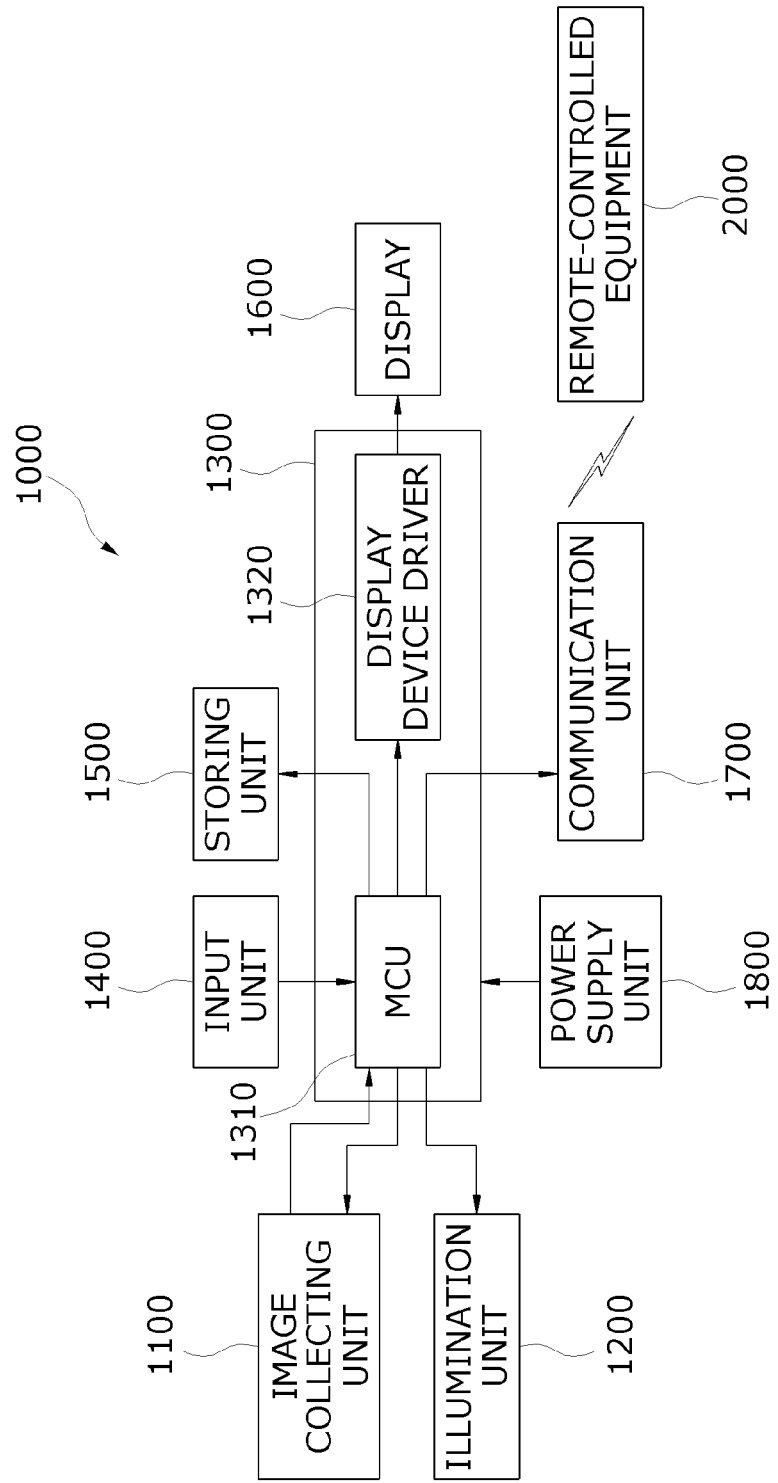
FIG. 1 is a block diagram of a configuration of an endoscopic apparatus according to the present invention.

FIG. 1 is a block diagram of a configuration of an endoscopic apparatus according to the present invention.

Referring to FIG. 1, an endoscopic apparatus 1000 according to the present invention includes an image collecting unit 1100, an illumination unit 1200, and a controller 1300.

The image collecting unit 1100 collects a real image and a thermal image of the inside of an object by using a tube (scope) and transmits the collected real image and thermal image to the controller 1300.

To this end, the image collecting unit 1100 includes an infrared (IR) block filter, a visible (VIS) image sensor, and a VIS image sensor board so as to collect the real image and includes an IR pass filter, an IR image sensor, and an IR image sensor board so as to collect the thermal image.

In addition, the image collecting unit 1100 may further include a focusing lens (convex lens) for radiating an image signal into an active area of the VIS image sensor and an active area of the IR image sensor, a Galvanometer for separating an image signal input from the object into a visible ray and an IR ray and splitting a path of the visible ray and a path of the IR ray in a direction of the VIS image sensor and in a direction of the IR image sensor, respectively, and a collimation lens for constantly radiating the image signal input from the object onto the Galvanometer or enlarging a view angle.

A detailed configuration of the image collecting unit 1100 will be described later with reference to FIG. 2.

The illumination unit 1200 radiates light onto the object so as to take a brighter real image. To this end, the illumination unit 1200 includes a light source, a light source control board, a focusing lens (convex lens) for condensing light emitted from the light source, a beam splitter for transmitting the light emitted from the light source to the outside, and a collimation lens for constantly radiating the light onto the beam splitter.

In the following embodiments, it is assumed that the light source is a halogen White Light Source (WLS). However, embodiments of the present invention are not limited thereto, and in various embodiments, the light source may be various types of wide-band light sources that emit a visible ray and a near IR ray each having a band of about 400 to 1,000 nm, such as a Solid State Light (SSL) source, Xenon arc, Mercury-Xenon arc, Quartz Tungsten-Halogen, etc.

The controller 1300 transmits a control signal used to control rotation of the Galvanometer to the image collecting unit 1100 so that the real image and the thermal image can be sequentially taken. Also, the controller 1300 processes the real image and the thermal image collected by using the image collecting unit 1100 in a user's desired shape and then outputs (displays) the processed real image and thermal image.

The controller 1300 may include a Micro Controller Unit (MCU) 1310 for analyzing the real image and the thermal image, and a display device driver 1320 for driving a display 1600 that displays the collected real image and thermal image, as illustrated in FIG. 1.

In various embodiments of the present invention, the endoscopic apparatus 1000 may further include an input unit 1400 for detecting the user's input for manipulation of the endoscopic apparatus 1000 to transmit the detected user's input to the controller 1300, a storing unit 1500 for storing the collected real image and thermal image, the display 1600 for displaying the real image and the thermal image transmitted from the controller 1300, a communication unit 1700 for transmitting the collected real image and thermal image to external other remote-controlled equipment (ex. a computer, a terminal, a mobile device, etc.) 2000 in a remote manner, and a power supply unit 1800 for applying power to components.

The input unit 1400 may include a button, a dial, a switch, etc. so as to receive the user's input for controlling the endoscopic apparatus 1000. Alternatively, the input unit 1400 may be a touch panel for detecting the user's touch input. In this case, the touch panel may be coupled to the display 1600 and thus may be a touch display. In an embodiment, the input unit 1400 may include a button that receives input for controlling on/off of the endoscopic apparatus 1000, image capturing, etc., and handpiece.

The display 1600 may be a Liquid Crystal Display (LCD) panel.

In various embodiments of the present invention, the communication unit 1700 may include at least one module for supporting a data transmission protocol so as to perform wired/wireless communication. The data transmission protocol may include near or remote wired/wireless communication protocols, such as Bluetooth, ZigBee, Wireless Fidelity (Wi-Fi), Long Term Evolution (LTE), third-Generation (3G), Universal Serial Bus (USB), etc.

Figure 2:
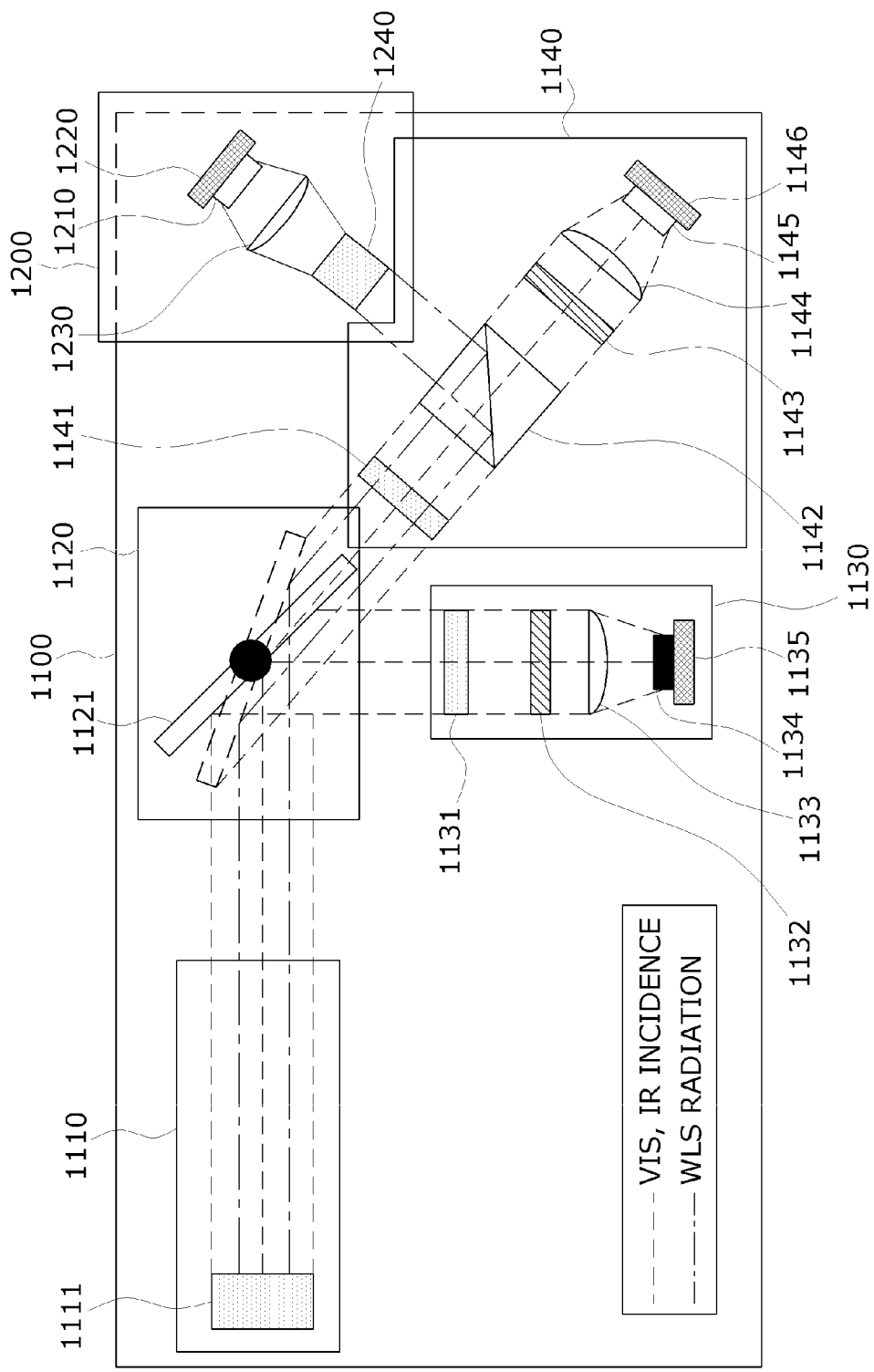
FIG. 2 is a view showing a detailed configuration of an image collecting unit and an illumination unit according to a first embodiment of the present invention.
Figure 3A:
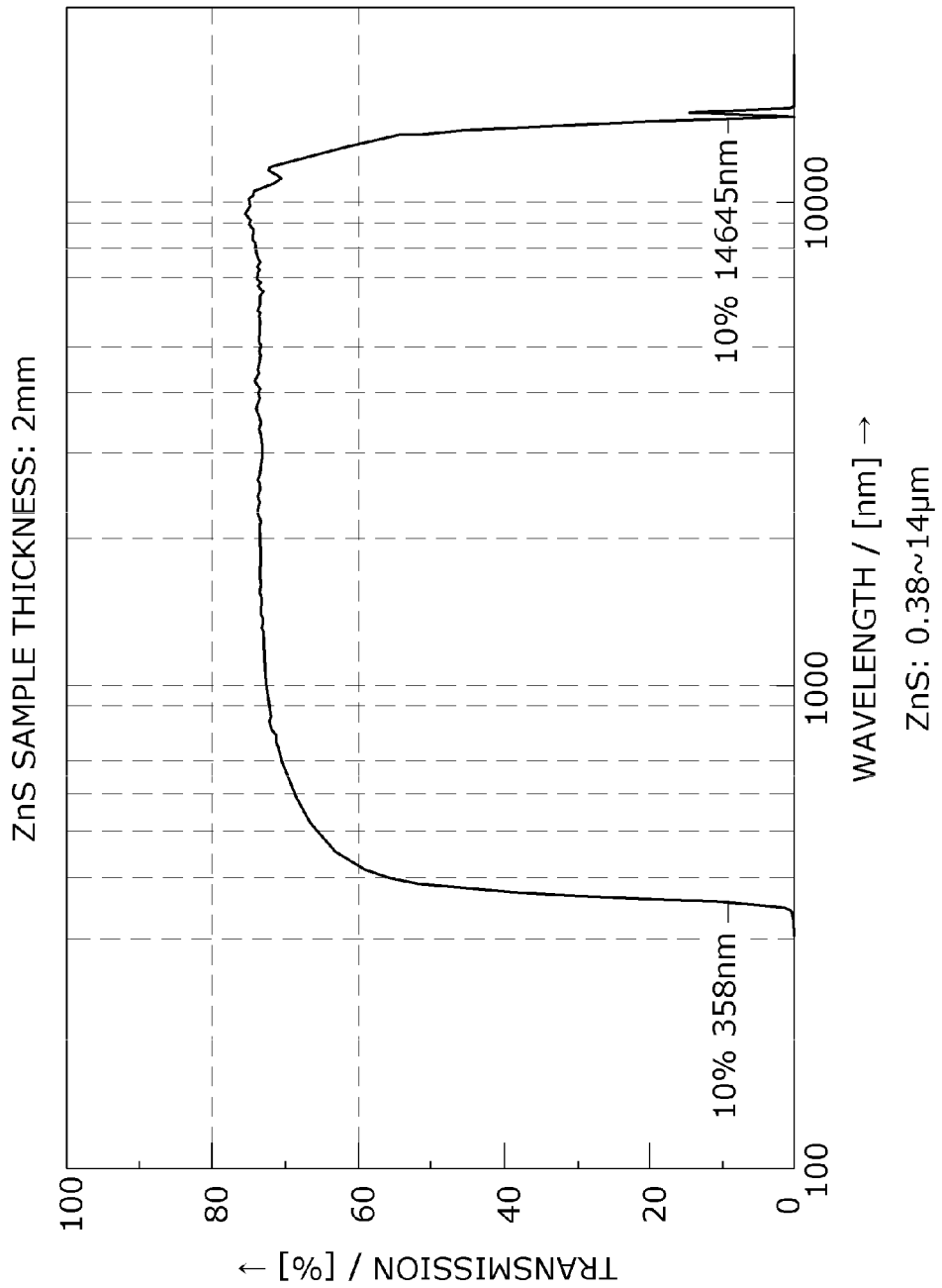
Figure 3B:
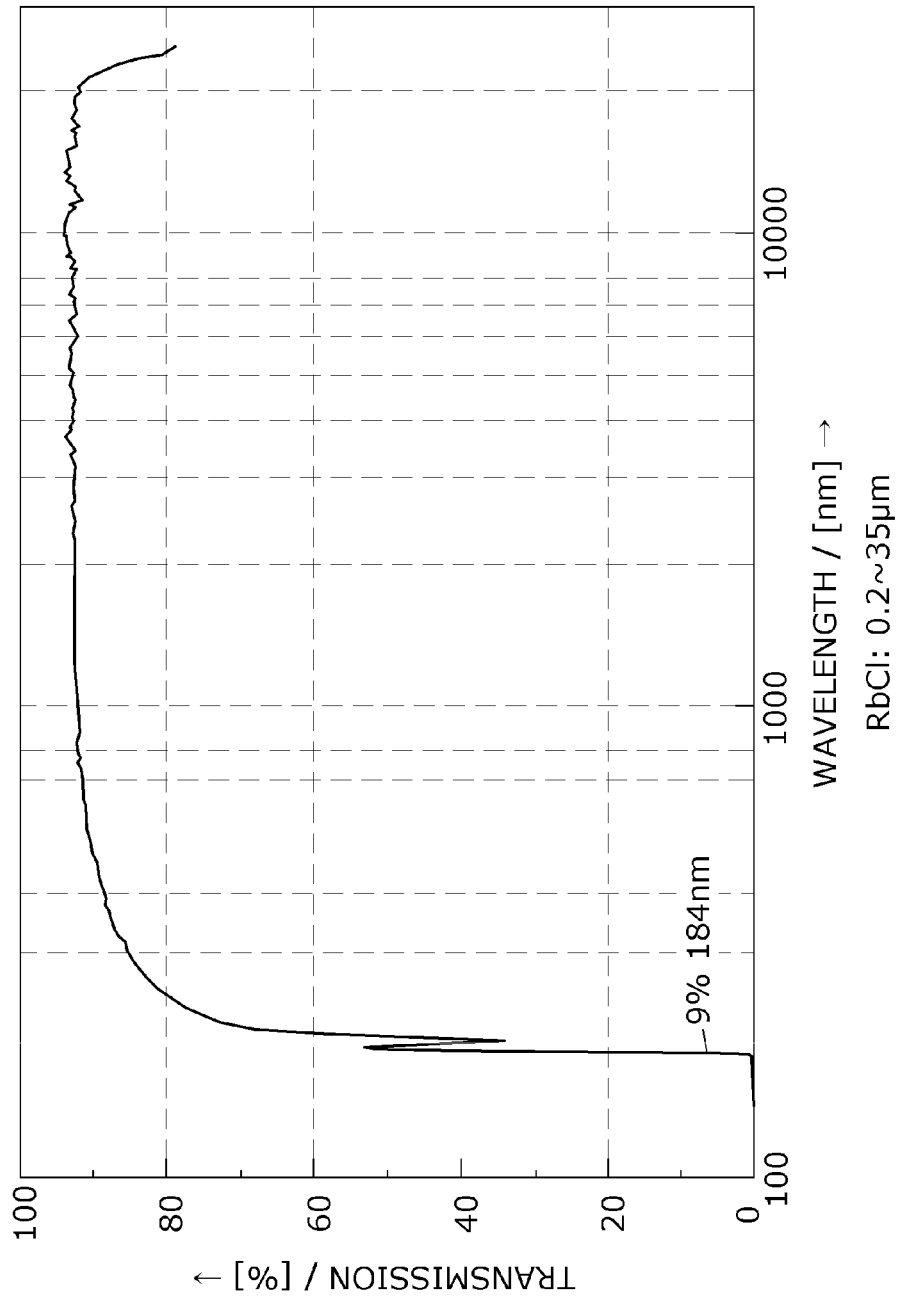
Figure 3C:
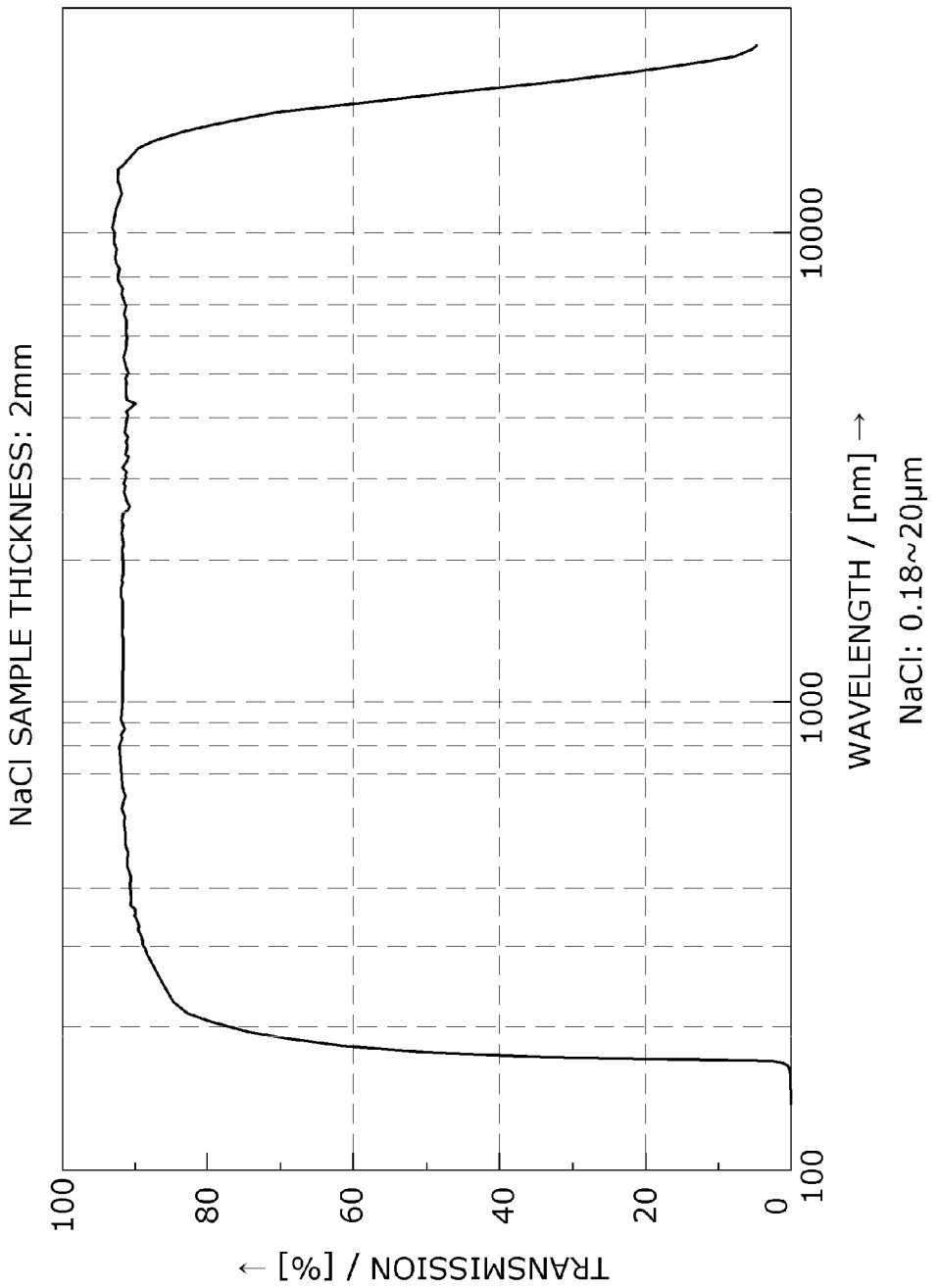

FIG. 2 is a view of a detailed configuration of an image collecting unit and an illumination unit according to the first embodiment of the present invention.

In various embodiments of the present invention, the image collecting unit 1100 collects a real image from a visible ray that constitutes an image signal, and collects a thermal image from an IR ray. To this end, in the first embodiment of the present invention, the image collecting unit 1100 includes a tube (scope) 1110, a splitting unit 1120, a thermal image collecting unit 1130, and a real image collecting unit 1140.

A first collimation lens 1111 is provided at an entrance part of the tube 1110. The image signal output from the object is incident on the first collimation lens 1111.

The incident image signal is a light signal including the visible ray and the IR ray. Thus, the first collimation lens 1111 has to be a lens through which both the visible ray and the IR ray can pass. The first collimation lens 1111 may include materials, such as zinc sulfide (ZnS), rubidium chloride (RbCl), chloride sodium (NaCl), barium fluoride ($BaF_2$), sodium fluoride (NaF), and potassium bromide (KBr), as illustrated in FIG. 3A to FIG. 3F. FIG. 3A to FIG. 3F is a view of transmission curves of ZnS, RbCl, NaCl, $BaF_2$, NaF, and KBr, which are examples of materials having good transmission characteristics in a visible ray band and an IR band. The first collimation lens 1111 may include various materials having good transmission characteristics in a band of 0.4 to 15 µm as well as the above-described materials.

In addition, when the diameter of the tube (scope) 1110 is small, the view angle of the first collimation lens 1111 is reduced so that an observation area of the object that may be observed by using the endoscopic apparatus 1000 may be reduced. Thus, the first collimation lens 1111 may be a wide angle lens having a wide view angle.

The splitting unit 1120 reflects the image signal to control a path of the image signal, and enables the image signal having the changed path to be transmitted to the thermal image collecting unit 1130 or the real image collecting unit 1140. To this end, the splitting unit 1120 may be a Galvanometer.

Figure 4:
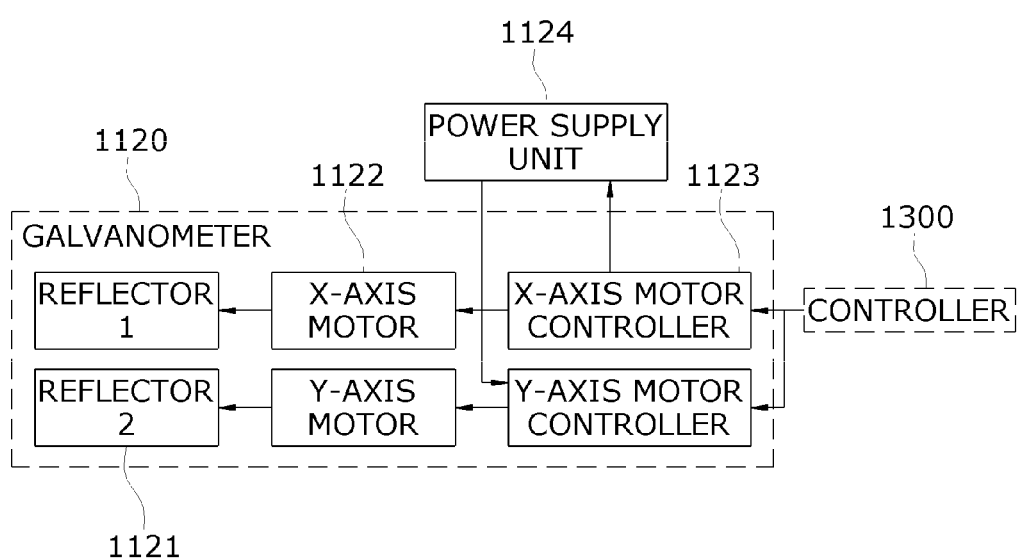
FIG. 4 is a block diagram of a configuration of a Galvanometer according to the first embodiment of the present invention.

The Galvanometer includes a reflector 1121 that may change an optical path by reflecting an image signal, a motor 1122 that is coupled to the reflector 1121 and rotates the reflector 1121, a motor controller 1123 that controls rotation of the motor 1122 based on a control signal of the controller 1300, and a power supply unit 1124 that supplies power to the motor 1122, as illustrated in FIG. 4. In various embodiments, the Galvanometer may include a plurality of reflectors, and a motor and a motor controller, which correspond to each of the plurality of reflectors, as illustrated in FIG. 4. The reflector 1121 may have a multi-axis movement path according to the number of combined reflectors.

Figure 5:
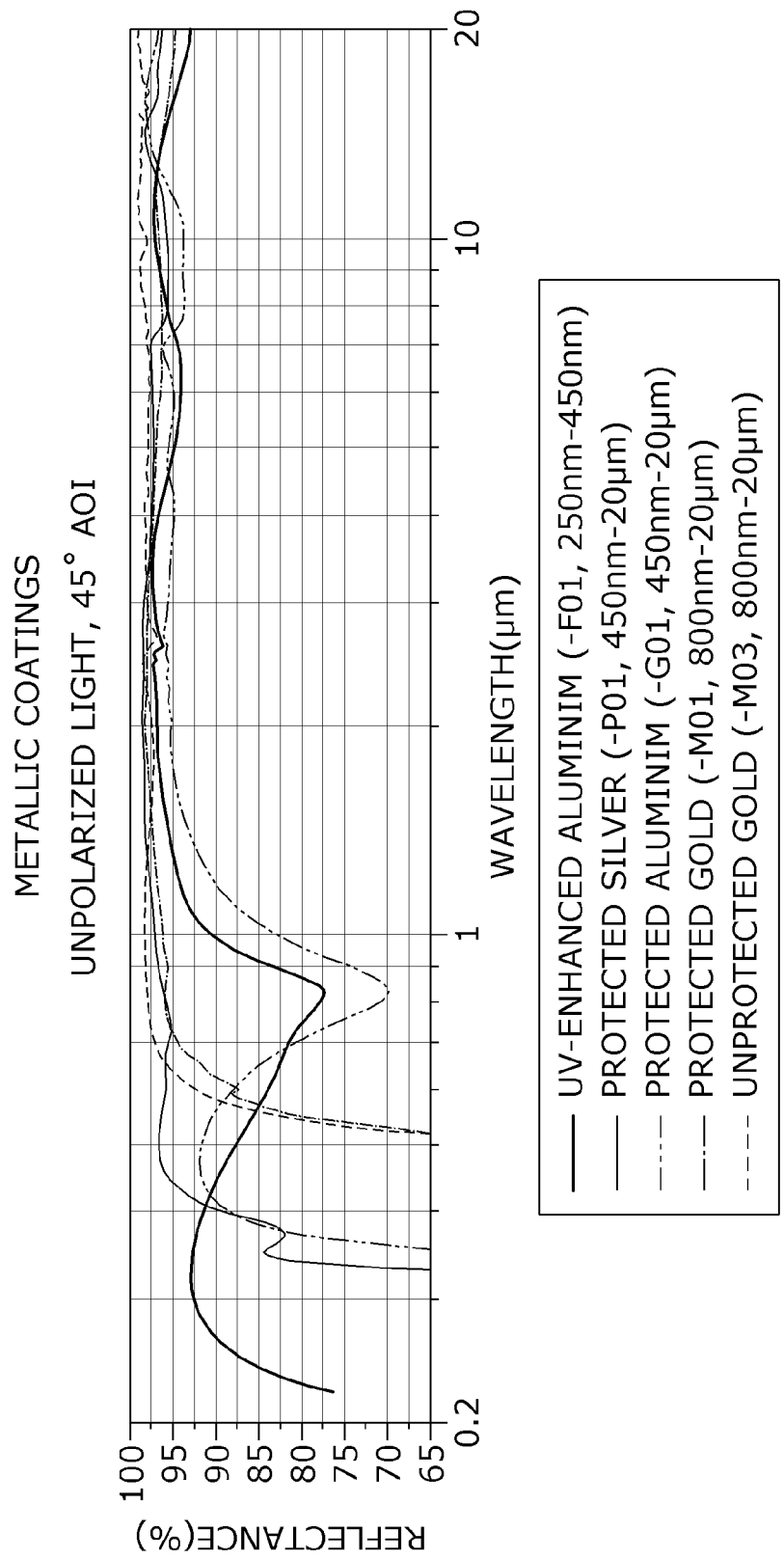
FIG. 5 is a graph showing reflectance of several materials that may be coated on a reflecting surface of a reflector.

Various materials that may reflect the image signal may be coated on a reflecting surface of the reflector 1121. FIG. 5 illustrates examples of materials that may be coated on the reflecting surface, and reflectance of the corresponding materials. Because the reflector 1121 has to reflect the image signal including a visible ray having a band of 400 to 700 nm and an IR ray having a band of 7,000 to 15,000 nm, protected silver or protected aluminum may be coated on the reflecting surface of the reflector 1121 by referring to reflectance illustrated in FIG. 3A to FIG. 3F.

Figure 6:
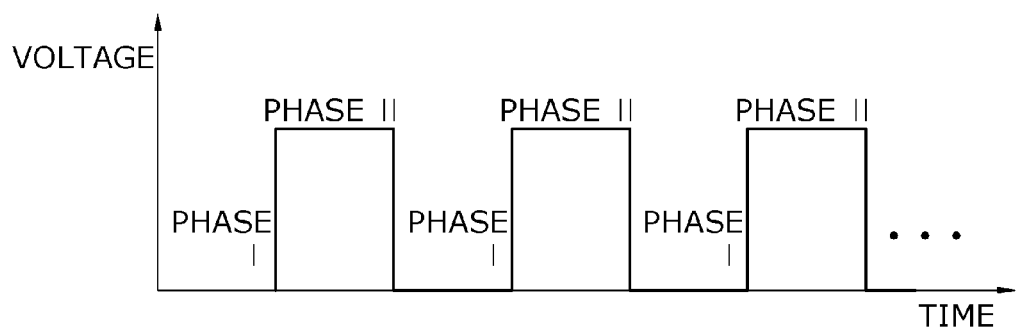
FIG. 6 is a graph showing an example of a voltage change of a control signal according to time in the first embodiment of the present invention.

The motor 1122 rotates at a predetermined angle according to the control signal received from the controller 1300. An angle between the reflecting surface of the reflector 1121 and an incidence path of the image signal varies according to rotation of the motor 1122. In detail, the motor 1122 rotates in such a way that the angle between the reflecting surface of the reflector 1121 and the incidence path of the image signal corresponds to a first mode (Phase 1) or a second mode (Phase 2) according to a voltage of the control signal received from the controller 1300, as illustrated in FIG. 6.

In various embodiments of the present invention, the controller 1300 changes the voltage of the control signal according to a preset period so that the angle between the reflecting surface of the reflector 1121 and the incidence path of the image signal is repeated alternately in the first mode and in the second mode. For example, the controller 1300 may repeatedly apply a control signal of 0V for the first mode and a control signal of 5V for the second mode to the motor 1122. As a changing period of the voltage of the control signal is decreased, the collecting speed of the thermal image and the real image may be increased. However, the change period may be determined to a proper length in consideration of a processing speed of the image sensor.

In various embodiments of the present invention, the Galvanometer may include a microelectromechanical systems (MEMS) mirror including a combined MEMS actuator and reflector. In this case, the reflector may have a one-axis or two-axis movement path according to a coupling method.

The image signal that passes through the first collimation lens 1111 is transmitted to the Galvanometer. The image signal transmitted to the Galvanometer is reflected on the reflecting surface of the reflector 1121. In this case, when the angle between the reflecting surface of the reflector 1121 and the incidence path of the image signal varies according to rotation of the reflector 1121, the image signal is transmitted to the thermal image collecting unit 1130 or the real image collecting unit 1140 according to an angle.

Figure 7:
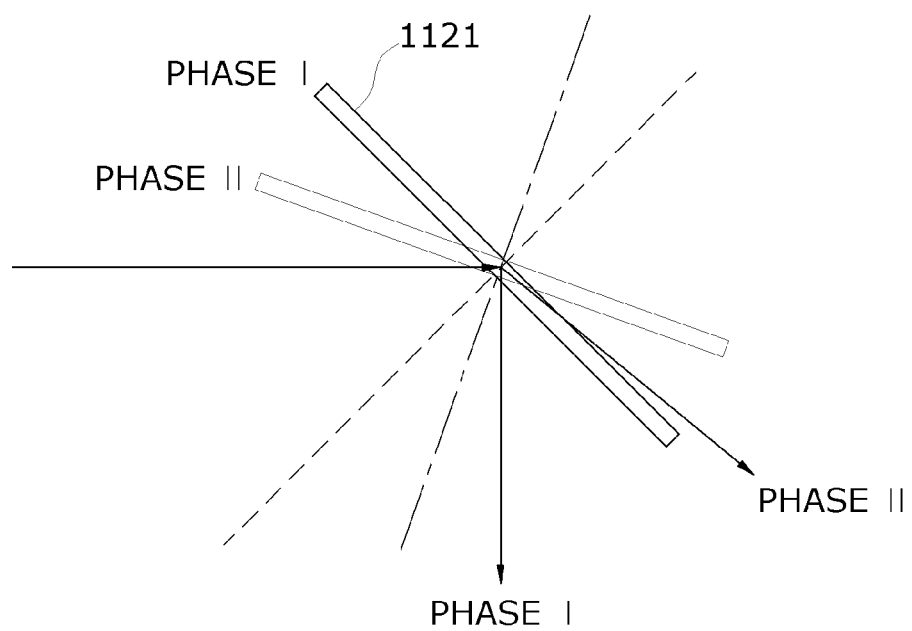
FIG. 7 is a view of a path on which an image signal is transmitted in each mode according to the first embodiment of the present invention.
Figure 9B:
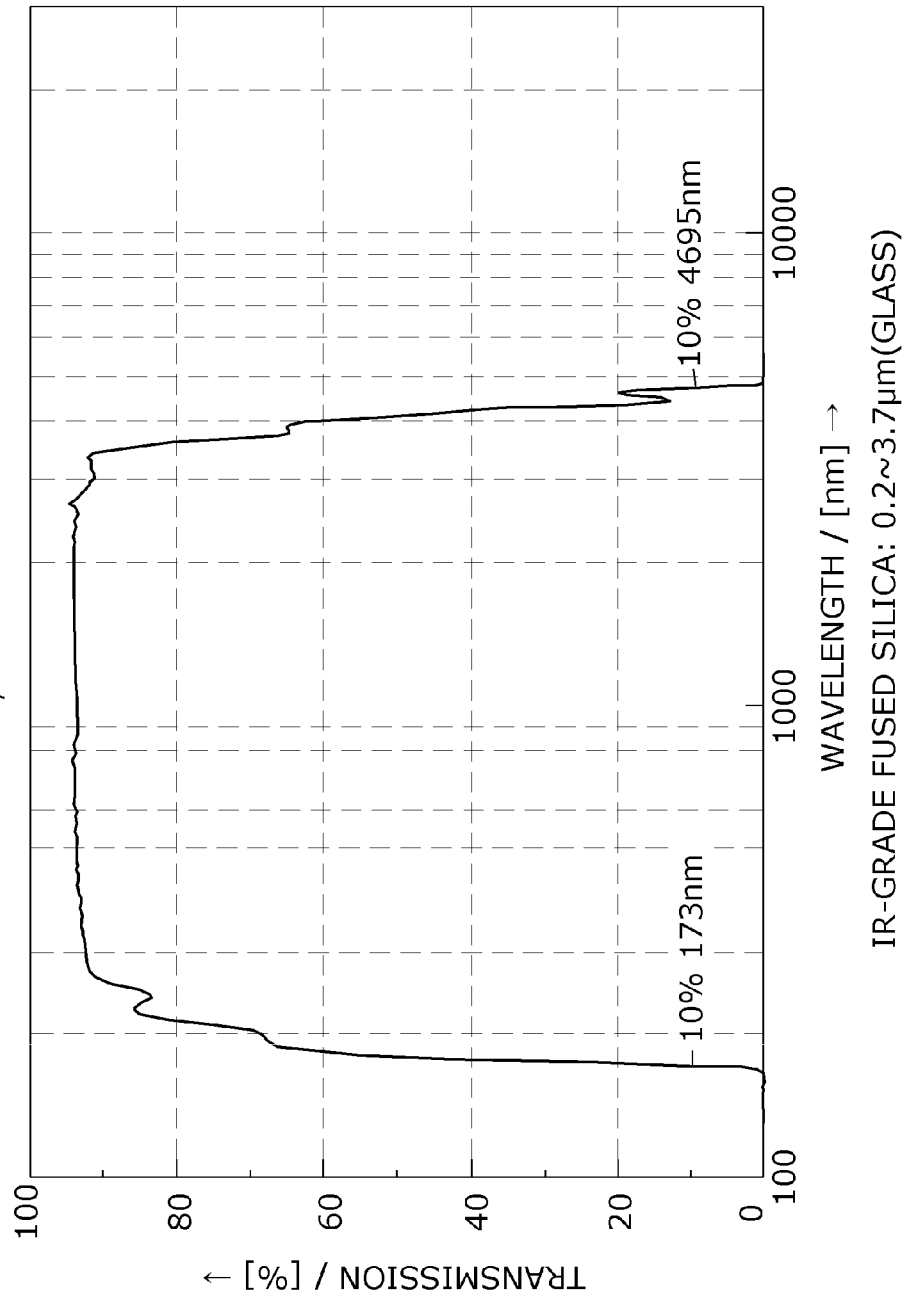
Figure 9C:
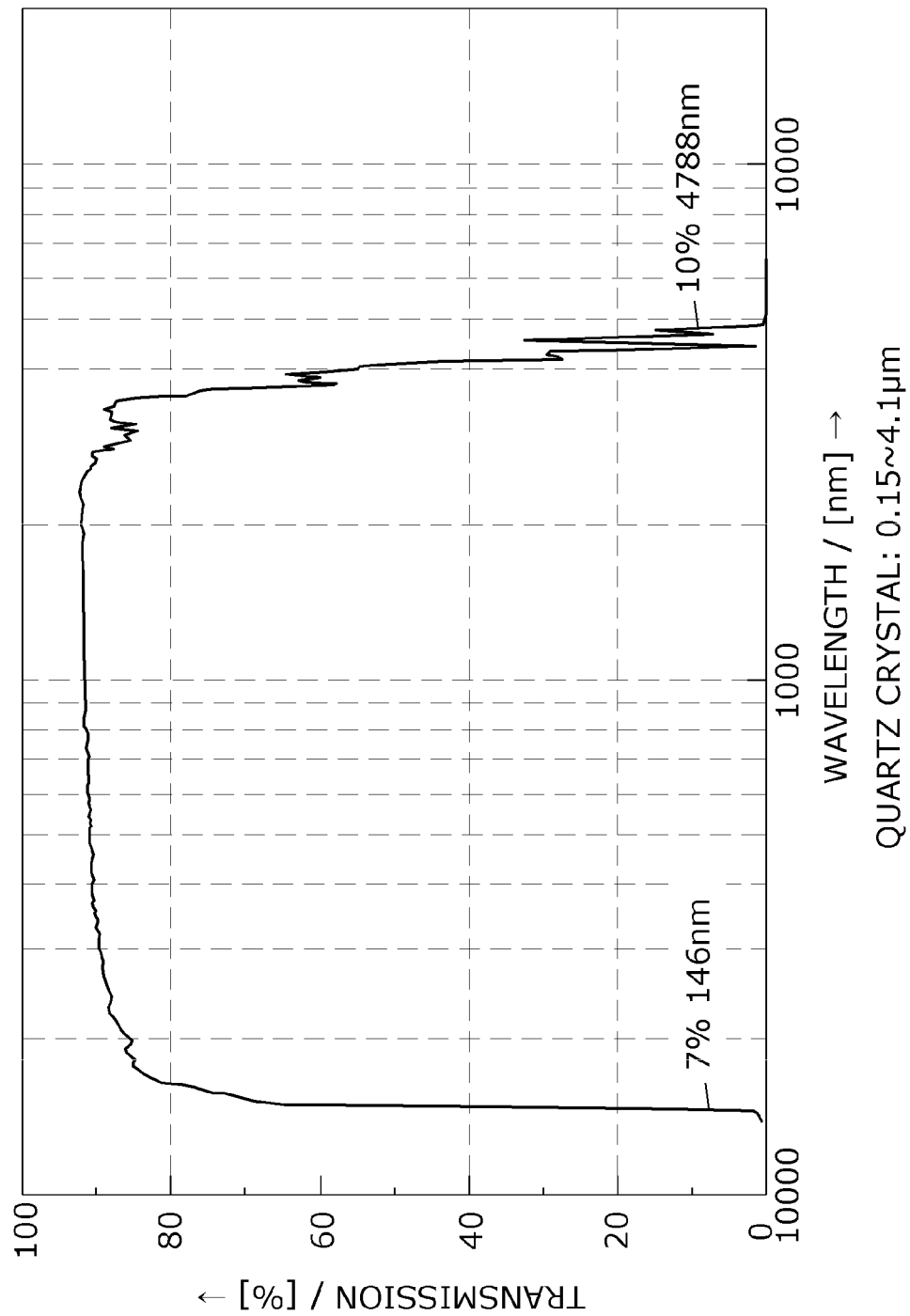
Figure 9D:
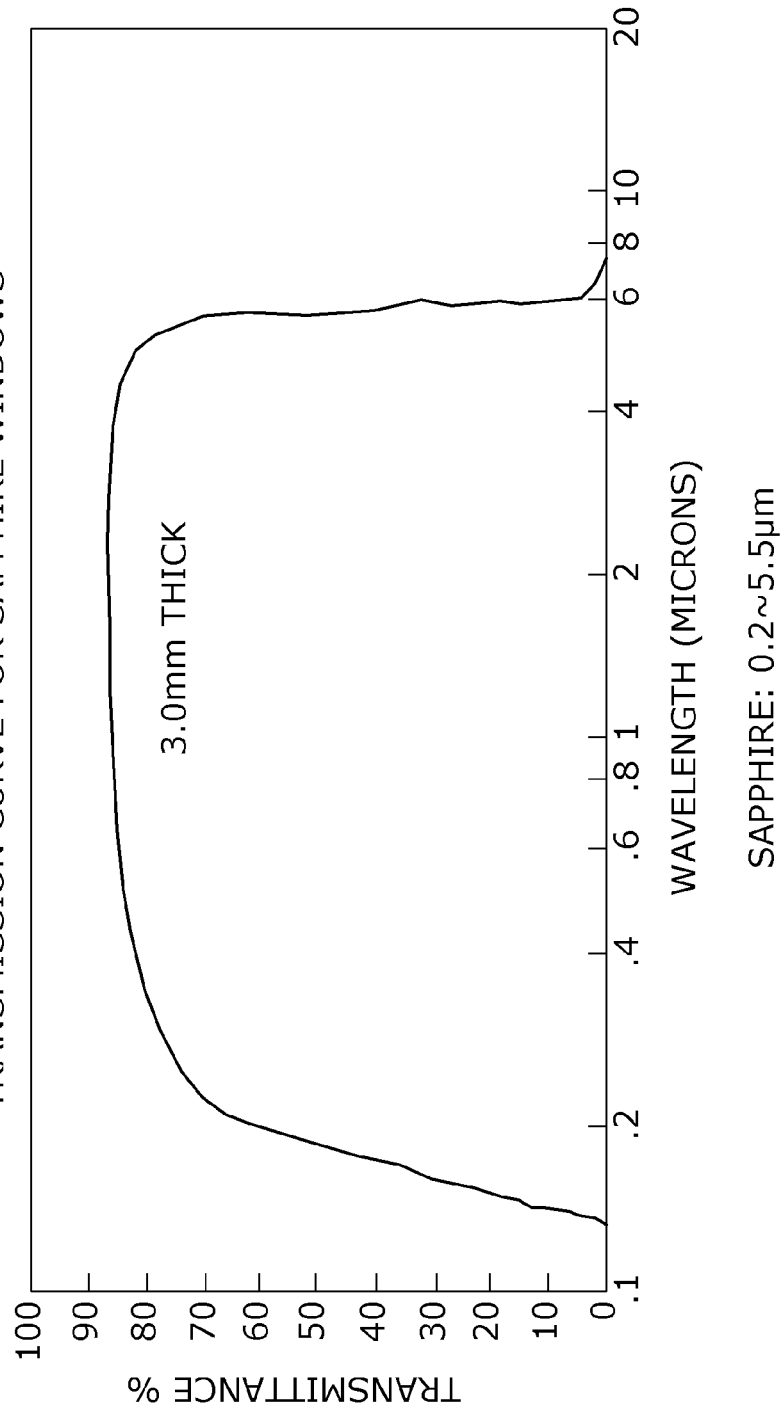
Figure 9E:
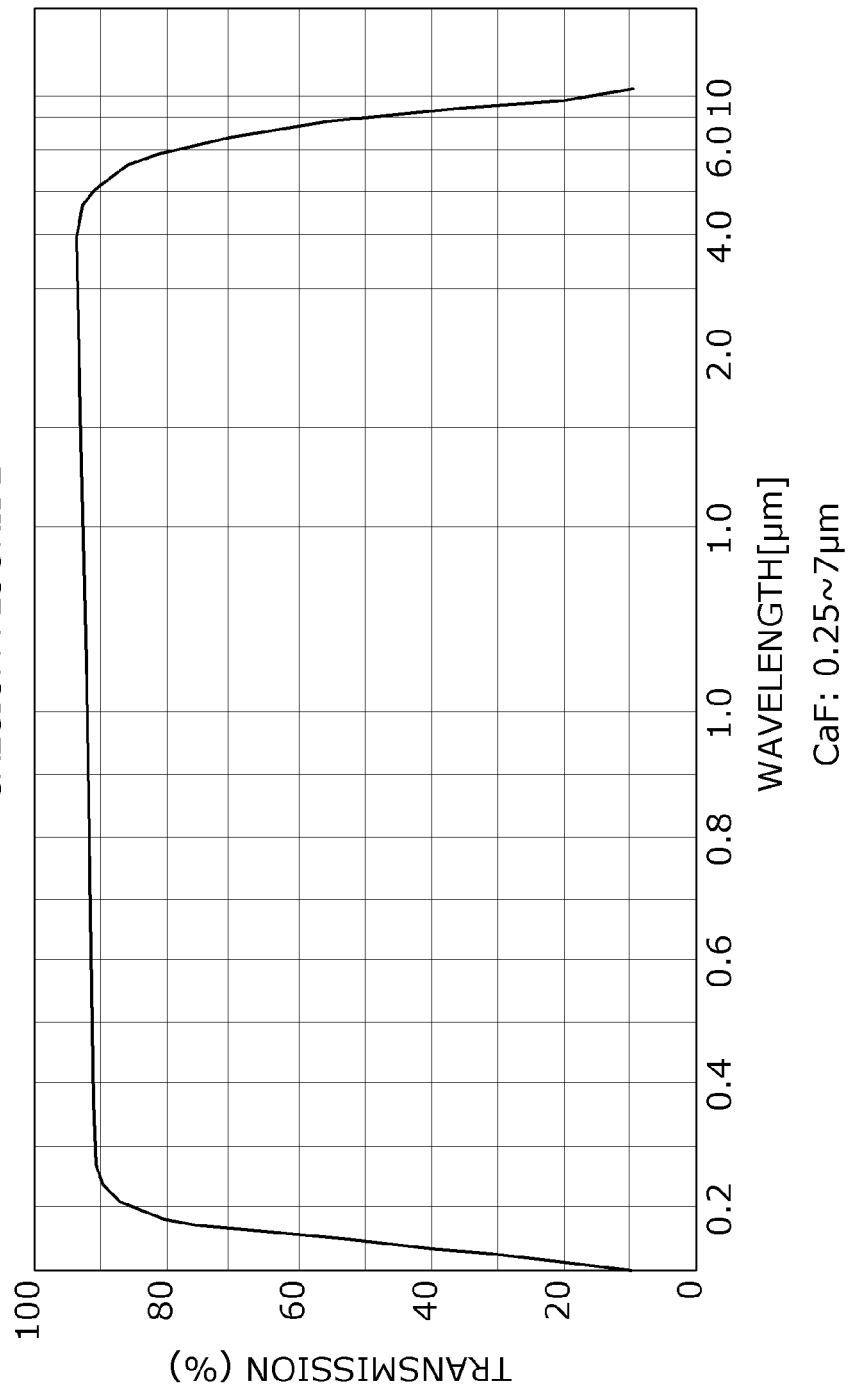

In an embodiment, the image signal may be transmitted to the thermal image collecting unit 1130 in the first mode and to the real image collecting unit 1140 in the second mode, as illustrated in FIG. 7.

The thermal image collecting unit 1130 collects a thermal image of the object from the image signal. The image signal transmitted to the thermal image collecting unit 1130 in the first mode passes through a second collimation lens (IR ray unit) 1131 and is condensed. The second collimation lens 1131 may be formed of a material through which both the visible ray and the IR ray may pass, for example, ZnS, RbCl, NaCl, $BaF_2$, NaF, and KBr, as illustrated in FIG. 3A to FIG. 3F. Alternatively, the second collimation lens 1131 may be formed of a material through which only the IR ray passes selectively, for example, germanium (Ge), silicon (Si), zinc selenide (ZnSe), as illustrated in FIG. 8A to FIG. 8C.

FIG. 8A to FIG. 8C is a view showing transmission curves of several materials having good transmission characteristics in the infrared band, for example, Ge, Si, and ZnSe. The second collimation lens 1131 may be formed of various materials having good transmission characteristics in a band of 7 to 15 µm as well as the above-described materials.

The image signal that passes through the second collimation lens 1131 is transmitted to an IR image sensor 1134 in a state in which the image signal passes through an IR pass filter 1132 and a first focusing lens 1133 and from which an unnecessary visible ray is removed, i.e., in a state in which only the IR ray remains. To this end, the IR pass filter 1132 and the first focusing lens 1133 may be formed of a material through which only the IR ray passes selectively, for example, Ge, Si, and ZnSe, as illustrated in FIG. 8A to FIG. 8C.

The IR pass filter 1132 and the first focusing lens 1133 may be formed of various materials having good transmission characteristics in the band of 7 to 15 μm as well as the above-described materials.

The IR image sensor 1134 may be mounted on an IR image sensor board 1135. When the IR image sensor 1134 detects the intensity of a photon per pixel and transmits the detected intensity to the IR image sensor board 1135, the IR image sensor board 1135 converts the intensity into an electrical signal and transmits the electrical signal to the controller 1300. The controller 1300 converts the received electrical signal into a thermal image.

The real image collecting unit 1140 collects a real image of the object from the image signal. The image signal transmitted to the real image collecting unit 1140 in the second mode passes through a third collimation lens (visible ray unit) 1141 and is condensed. The third collimation lens 1141 may be formed of a material through which both the visible ray and the IR ray may pass, for example, ZnS, RbCl, NaCl, BaF$_2$, NaF, and KBr illustrated in FIG. 3A to FIG. 3F. Alternatively, the third collimation lens 1141 may be formed of a material through which only the visible ray may pass selectively, for example, BK7, fused silica, crystal quartz, calcium fluoride (CaF$_2$), magnesium fluoride (MgF$_2$), and sapphire, as illustrated in FIG. 9A to FIG. 9F.

The image signal that passes through the third collimation lens 1141 is transmitted to a VIS image sensor 1145 in a state in which the image signal passes through a wavelength-independent beam splitter 1142, an IR block filter 1143 and a second focusing lens 1144 and from which an unnecessary IR ray is removed, i.e., in a state in which only the visible ray remains. The wavelength-independent beam splitter 1142 has constant reflectance and transmittance. In an embodiment, when the wavelength-independent beam splitter 1142 has reflectance of 30% and transmittance of 70%, 70% of the visible ray is transmitted. In various embodiments, the wavelength-independent beam splitter 1142 may have various reflectance and transmittance according to a user's purpose. The IR block filter 1143 and the second focusing lens 1144 may be formed of a material through which only the visible ray may pass selectively, for example, BK7, fused silica, crystal quartz, CaF$_2$, MgF$_2$, and sapphire, as illustrated in FIG. 9A to FIG. 9F.

The VIS image sensor 1145 may be mounted on a VIS image sensor board 1146. When the VIS image sensor 1145 detects the intensity of lights R(Red), G(Green) and B(Blue) per pixel and transmits the detected intensity of the lights R, G and B to the VIS image sensor board 1146, the VIS image sensor board 1146 converts the intensity into electrical signals and transmits the electrical signals to the controller 1300. The controller 1300 converts the received electrical signals into a real image.

In various embodiments of the present invention, the endoscopic apparatus 1000 may further include the illumination unit 1200.

The illumination unit 1200 includes a light source 1210 for radiating light onto the object so that the object can be observed more brightly. FIG. 2 illustrates an example in which a halogen white light source is used as the light source 1210. The light source 1210 is controlled to emit light by using a light source control board 1220. The light source control board 1220 controls the light source 1210 according to the control signal received from the controller 1300.

A focus of the light emitted from the light source 1210 is controlled by using a third focusing lens 1230, is coupled to a fourth collimation lens 1240 to be condensed, and is transmitted to the wavelength-independent beam splitter 1142 of the real image collecting unit 1140.

In this case, because the third focusing lens 1230 and the fourth collimation lens 1240 have to transmit the light of the visible ray band and the near IR band (400 to 900 nm), the third focusing lens 1230 and the fourth collimation lens 1240 may be formed of a material such as ZnS, RbCl, NaCl, BaF$_2$, NaF, and KBr illustrated in FIG. 3A to FIG. 3F or a material such as BK7, fused silica, crystal quartz, CaF$_2$, MgF$_2$, and sapphire illustrated in FIG. 9A to FIG. 9F.

Only part of the light transmitted to the wavelength-independent beam splitter 1142 is reflected according to reflectance and transmittance of the wavelength-independent beam splitter 1142. The reflected light is transmitted to the Galvanometer and is radiated onto the object through the tube 1110 in the second mode. In an embodiment, when the wavelength-independent beam splitter 1142 has reflectance of 30% and transmittance of 70%, 30% of the light emitted from the light source 1210 is radiated onto the object.

In various embodiments of the present invention, anti-reflection (AR) coating may be applied to the wavelength-independent beam splitter 1142, a lens, and filters so as to prevent a phenomenon that, when the image signal (light) passes through the wavelength-independent beam splitter 1142, the lens and the filters, part of the image signal (light) may be reflected on surfaces thereof.

Figure 10:
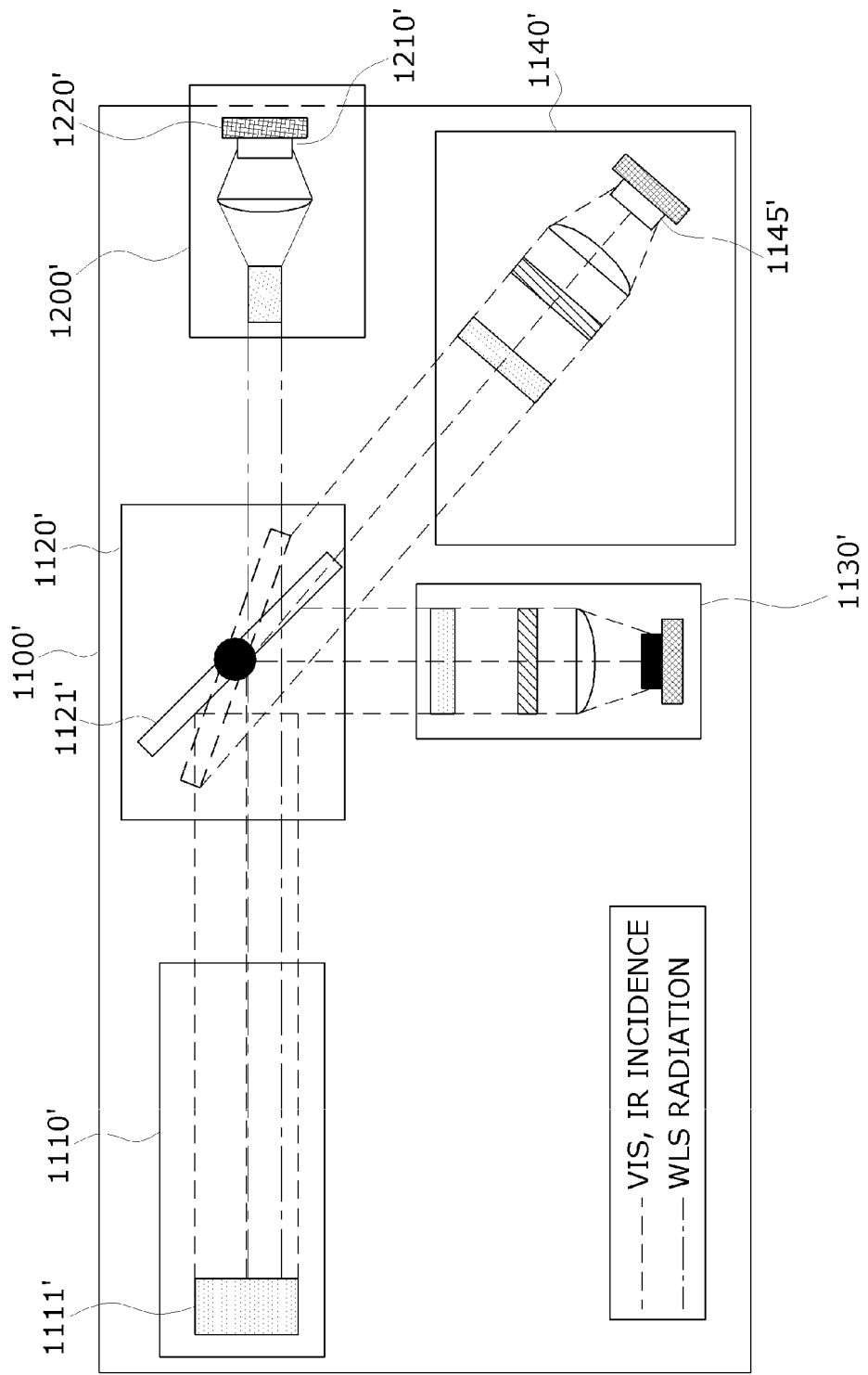
FIG. 10 is a view of a detailed configuration of an image collecting unit and an illumination unit according to a second embodiment of the present invention.

FIG. 10 is a view of a detailed configuration of an image collecting unit and an illumination unit according to a second embodiment of the present invention.

In the second embodiment of the present invention, an image collecting unit 1100' and an illumination unit 1200' have a structure in which light emitted from a light source 1210' of the illumination unit 1200' is radiated onto the object via a separate path without passing through a real image collecting unit 1140', as in the first embodiment. To this end, in the second embodiment of the present invention, the Galvanometer is configured to further implement a third mode. In this case, the illumination unit 1200' may be provided collinearly with respect to an entrance part of a first collimation lens 1111'. Also, in this case, the real image collecting unit 1140' may not include the wavelength-independent beam splitter 1142.

Figure 11:
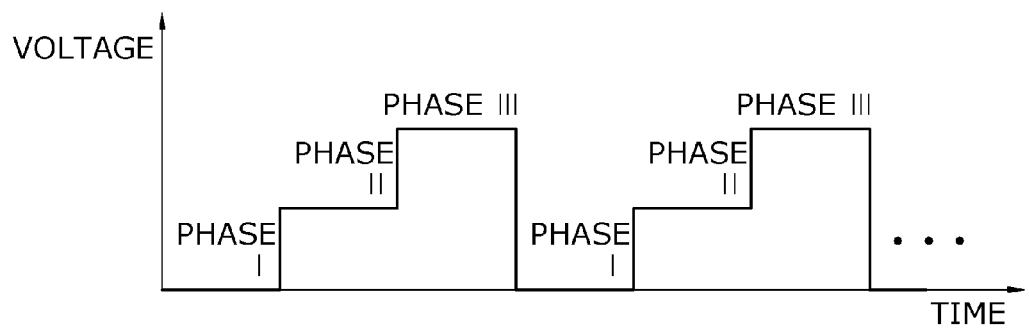
FIG. 11 is a graph showing an example of a voltage change of a control signal according to time in the second embodiment of the present invention.
Figure 12:
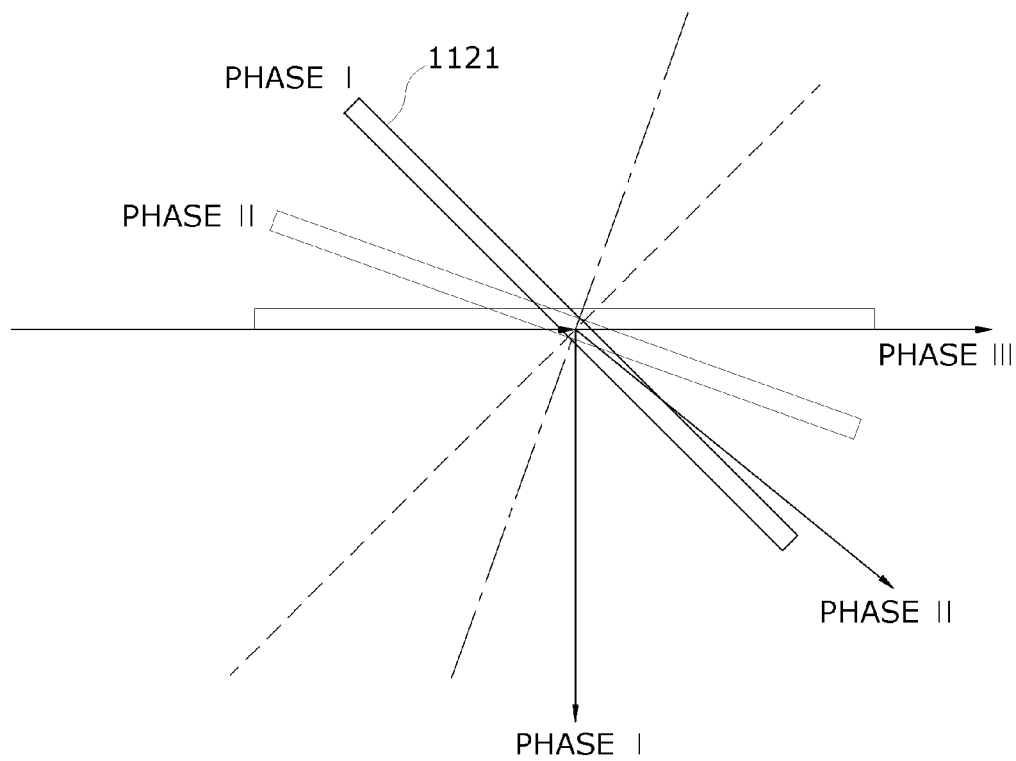
FIG. 12 is a view showing a path on which an image signal and light are transmitted in each mode according to the second embodiment of the present invention.

In detail, in the second embodiment, a reflector 1121' of the Galvanometer rotates to correspond to the first mode (Phase 1), the second mode (Phase 2), or the third mode (Phase 3) according to the voltage of the control signal received from the controller 1300. The controller 1300 changes the voltage of the control signal according to a preset period so that the angle between the reflecting surface of the reflector 1121' and the incidence path of the image signal is repeated alternately in the first through third modes, as illustrated in FIG. 11.

The image signal is transmitted to a thermal image collecting unit 1130' in the first mode and is transmitted to the real image collecting unit 1140' in the second mode, and light emitted from the light source 1210' is reflected by the reflector 1121' and is not radiated onto the object in the first mode and the second mode. Because the movement path of the light emitted from the light source 1210' and the reflecting surface of the reflector 1121' are horizontal with respect to each other in the third mode, the light emitted from the light source 1210' is radiated onto the object directly via an entrance part of a tube 1110'.

According to the second embodiment of the present invention, the real image collecting unit 1140' and the illumination unit 1200' are separated from each other. Thus, unlike in the first embodiment, the wavelength-independent beam splitter 1142 is not required, the whole of the visible ray separated from the image signal is transmitted to be transferred to a VIS image sensor 1145', and the whole of the light emitted from the illumination unit 1200' can be radiated onto the object.

The description of other configurations of FIG. 10 is the same as that of the first embodiment and thus will be omitted.

Figure 13A:
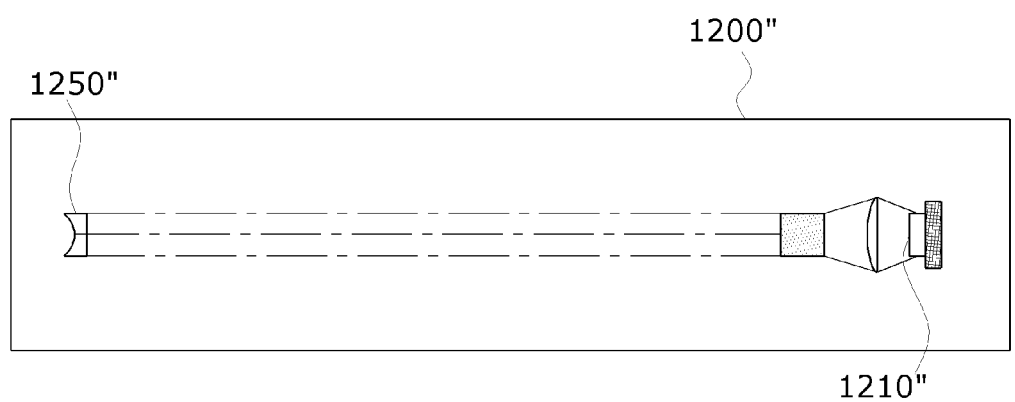
FIG. 13A to FIG. 13B is a view showing a detailed configuration of an image collecting unit and an illumination unit according to a third embodiment of the present invention.
Figure 13B:
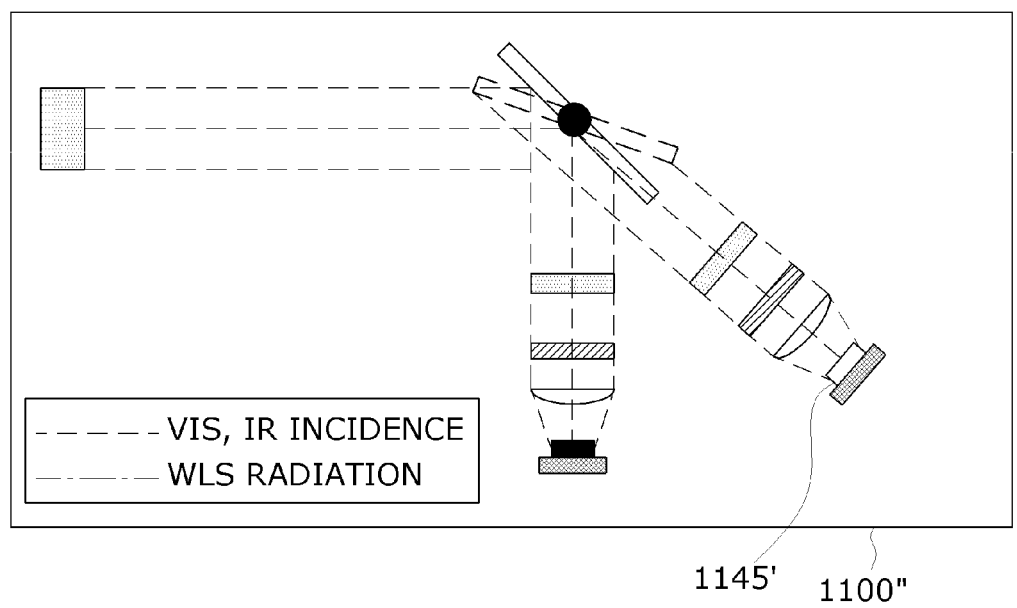

FIG. 13A to FIG. 13B is a view of showing a detailed configuration of an image collecting unit and an illumination unit according to a third embodiment of the present invention;

In the third embodiment of the present invention, an image collecting unit 1100" and an illumination unit 1200" are separated from each other. In this case, optical arrangement and transmission is performed in a free space. A concave lens 1250" may be further provided at an output terminal of the illumination unit 1200".

According to the third embodiment of the present invention, the image collecting unit 1100" and the illumination unit 1200" are separated from each other. Thus, unlike in the first embodiment, the wavelength-independent beam splitter 1142 is not required, and additional optical path configuration and optical arrangement is required. Although additional optical path configuration and optical arrangement is required, a radiation position and a radiation method of a light source 1210" may be diverse to be suitable for an observation purpose. Also, according to the third embodiment of the present invention, the visible ray and the IR in the image signal can be transmitted to image sensors, respectively, and the whole of light emitted from the illumination unit 1200" can be radiated onto the object.

The description of other configurations of FIG. 13A to FIG. 13B is the same as that of the first embodiment and thus will be omitted.

Figure 14A:
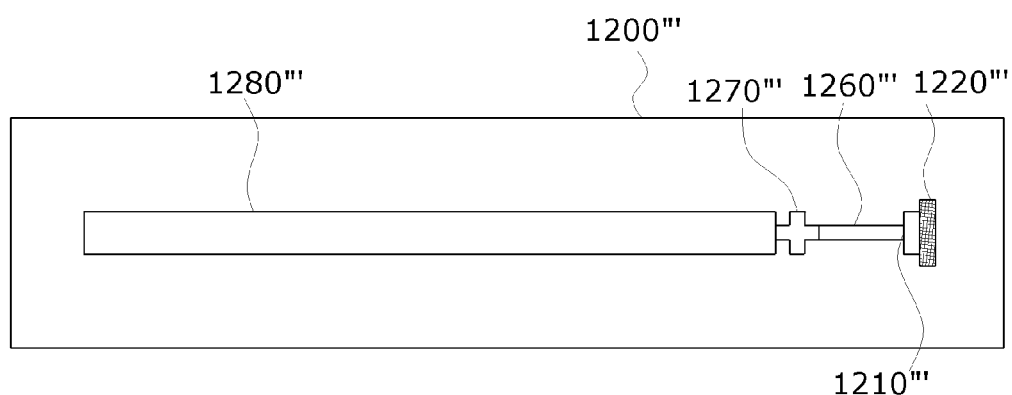
FIG. 14A to FIG. 14B is a view showing a detailed configuration of an image collecting unit and an illumination unit according to a fourth embodiment of the present invention.
Figure 14B:
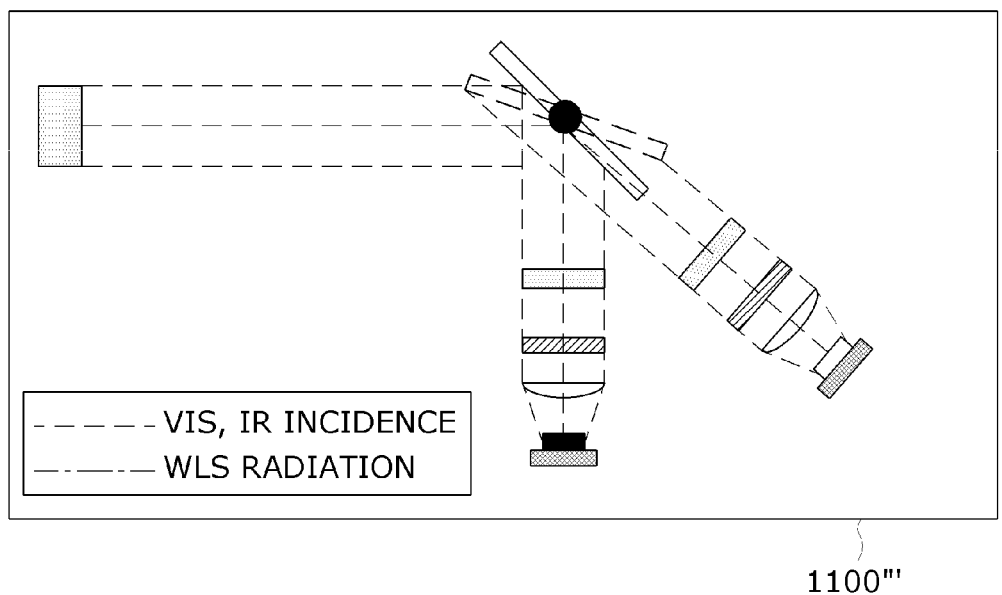

FIG. 14A to FIG. 14B is a view showing a detailed configuration of an image collecting unit and an illumination unit according to a fourth embodiment of the present invention.

In the fourth embodiment of the present invention, an image collecting unit 1100''' and an illumination unit 1200''' are separated from each other. In this case, the illumination unit 1200''' is delivered to the object via an optical fiber 1260''' and a connector 1270''' instead of the third focusing lens 1230 and the fourth collimation lens 1240. A light source 1210''' (light source chip) and a light source control board 1220''' are packaged in a single module, and an output unit of a module that constitutes the light source 1210''' is pig-tailed. Light emitted from the light source 1210''' is radiated onto the object via a light guide 1280''' by means of the optical fiber 1260''' and the connector 1270'''.

According to the fourth embodiment of the present invention, optical arrangement of the illumination unit 1200''' is not required. Thus, the illumination unit 1200''' can be easily attached to or detached from the endoscopic apparatus 1000.

Figure 15:
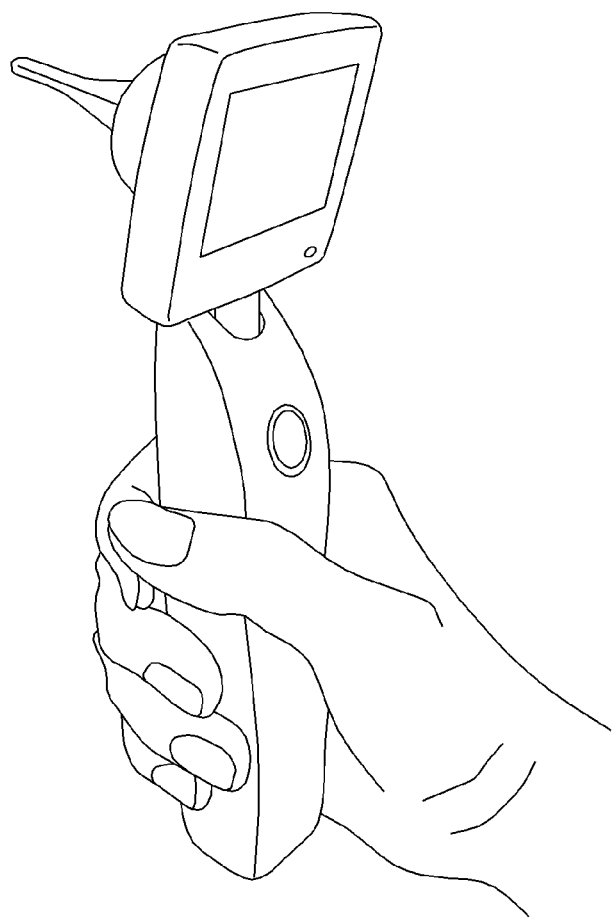
FIG. 15 is a view showing a real implementation example of the endoscopic apparatus according to the present invention.

FIG. 15 is a view showing a real implementation example of the endoscopic apparatus according to the present invention.

Referring to FIG. 15, the image collecting unit 1100, the illumination unit 1200, and the controller 1300 are packaged in a single apparatus. The tube 1110 to be inserted into the object, the input unit 1400, and the display 1600 for outputting the collected real image and thermal image may be provided outside the endoscopic apparatus 1000. The image collecting unit 1100 and the illumination unit 1200 may be mounted inside the endoscopic apparatus 1000.

FIG. 15 shows an example of an appearance of the endoscopic apparatus 1000 according to the present invention, and the appearance of the endoscopic apparatus 1000 may be implemented in various shapes according to implementation.

As described above, in an endoscopic apparatus according to the present invention, a real image and a thermal image can be taken from an image signal inside an object, which is acquired from one tube (scope), sequentially at a high speed so that the diameter of an internal insertion tool (tube, scope) can be reduced and internal insertion and observation of the object can be easily performed.

In addition, in the endoscopic apparatus according to the present invention, a real image and a thermal image of an object can be simultaneously observed so that more objective and precise diagnosis can be performed on the object and early diagnosis can be performed using a simple screening method.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An endoscopic apparatus comprising:
    an image collecting unit comprising a thermal image collecting unit collecting a thermal image from an image signal of an object and a real image collecting unit collecting a real image from the image signal of the object;
    a controller transmitting a control signal to the image collecting unit so as to transmit the image signal to one of the thermal image collecting unit and the real image collecting unit according to a preset period; and
    a display displaying the collected thermal image and real image,
    wherein the image collecting unit comprises a splitting unit splitting an optical path of the image signal in a direction of one of the thermal image collecting unit and the real image collecting unit according to the control signal,
    wherein the thermal image collecting unit comprises an infrared (IR) image sensor, an IR pass filter along an optical path between the splitting unit and the IR image sensor, and a first focusing lens along the optical path between the IR image sensor and the splitting unit,
    wherein the IR pass filter is arranged to pass an IR ray in the image signal and the first focusing lens is arranged to focus the IR ray passed through the IR pass filter, and the IR image sensor is arranged to detect the IR ray focused by the first focusing lens,
    wherein the real image collecting unit comprises a visible (VIS) image sensor, an IR block filter arranged along an optical path between the VIS image sensor and the splitting unit, and a second focusing lens arranged along an optical path between the IR block filter and the VIS image sensor,
    wherein the IR block filter is arranged to block the IR ray in the image signal, the second focusing lens is arranged to focus the image signal having the IR ray blocked by the IR block filter, and the VIS image sensor is arranged to detect the image signal focused by the second focusing lens, wherein the real image collecting unit comprises:
a third collimation lens condensing the image signal; and
a VIS image sensor board converting the detected visible ray into an electrical signal and transmitting the electrical signal to the controller, wherein the splitting unit comprises:
a reflector changing the optical path of the image signal by reflecting the image signal;
a motor coupled to the reflector and rotating the reflector; and
a motor controller controlling rotation of the motor, wherein the motor controller controls rotation of the motor so that a reflecting surface of the reflector and an incidence path of the image signal form an angle corresponding to a first mode or second mode according to the control signal, and wherein the image signal is reflected by the reflecting surface and is transmitted to the thermal image collecting unit in the first mode and is reflected by the reflecting surface and is transmitted to the real image collecting unit in the second mode.

2. The endoscopic apparatus of claim 1, wherein the image collecting unit further comprises:
a tube inserted into the object.

3. The endoscopic apparatus of claim 2, wherein the tube comprises a first collimation lens condensing the image signal output from the object.

4. The endoscopic apparatus of claim 3, wherein the thermal image collecting unit comprises:
a second collimation lens condensing the image signal; and
an IR image sensor board converting the detected IR ray into an electrical signal and transmitting the electrical signal to the controller.

5. The endoscopic apparatus of claim 1, further comprising an illumination unit radiating light onto the object.

6. The endoscopic apparatus of claim 5, wherein the illumination unit comprises:
a light source emitting light;
a light source control board controlling the light source to emit the light;
a third focusing lens controlling a focus of the emitted light; and
a fourth collimation lens condensing the light that passes through the third focusing lens.

7. The endoscopic apparatus of claim 6, wherein the real image collecting unit further comprises a beam splitter having constant reflectance and transmittance, the beam splitter arranged between the second focusing lens and the splitting unit and transmitting a part of the image signal that passes through the third collimation lens to the IR block filter according to the transmittance, and
the illumination unit is configured so that a part of light passing through the fourth collimation lens is reflected by the beam splitter and is radiated onto the object in the second mode.

8. The endoscopic apparatus of claim 7, wherein the motor controller controls rotation of the motor according to the control signal so that the reflecting surface of the reflector and an emission path of the light between the illumination unit and the splitting unit are horizontal with respect to each other in a third mode, and the whole of the light from the illumination unit is radiated onto the object in the third mode.

9. The endoscopic apparatus of claim 8, wherein the illumination unit is separated from the image collecting unit, and the optical path of the image signal and an emission path of the light do not overlap each other.

10. The endoscopic apparatus of claim 9, wherein the illumination unit further comprises a concave lens provided at an output terminal thereof.

11. The endoscopic apparatus of claim 6, wherein the illumination unit comprises:
a light source emitting light;
a light source control board controlling the light source to emit the light;
a third focusing lens controlling a focus of the emitted light;
an optical fiber to which the light passing through the third focusing lens moves;
a connector provided at a distal end of the optical fiber; and
a light guide connected to the connector and radiating the light onto the object.

12. The endoscopic apparatus of claim 1, further comprising:
an input unit receiving a user's input for controlling the endoscopic apparatus;
a storing unit storing the collected thermal image and real image;
a communication unit for transmitting the collected thermal image and real image to external remote-controlled equipment; and
a power supply unit for applying power to the endoscopic apparatus.

13. The endoscopic apparatus of claim 1, wherein the splitter reflects both the IR rays in the image signal and visible light in the image signal,
the splitter reflects the IR rays and visible light in the image signal to the thermal image collecting unit,
the splitter reflects the IR rays and visible light in the image signal to the real image collecting unit, and
the splitter reflects the IR rays and visible light in the image signal to a respective one of the thermal image collecting unit and the real image collecting unit according to the control signal from the controller.

14. The endoscopic apparatus of claim 1, wherein the splitter reflects visible light in a band in a range from 400 to 700 nm and the splitter reflects IR light in a band in a range from 7,000 to 15,000 nm.

15. The endoscopic apparatus of claim 1, further comprising:
a light source,
wherein light from the light source is directed to the object, and light from the light source that has been reflected off of the object defines the image signal, and
wherein light from the light source passes through the splitter to reach the object.

16. The endoscopic apparatus of claim 15, wherein the splitter includes a reflector, and
wherein the light from the light source is reflected on a surface of the reflector to reach the object.

17. The endoscopic apparatus of claim 15, wherein the splitter includes a reflector arranged along a light path between the light source and the object, and
wherein the control signal controls the reflector to be arranged parallel to the light from the light source, such that the light from the light source bypasses the reflector to reach the object.

* * * * *